(12) United States Patent
Faltys et al.

(10) Patent No.: US 9,700,716 B2
(45) Date of Patent: Jul. 11, 2017

(54) NERVE CUFF WITH POCKET FOR LEADLESS STIMULATOR

(71) Applicant: SetPoint Medical Corporation, Valencia, CA (US)

(72) Inventors: Michael A. Faltys, Valencia, CA (US); Roy C. Martin, Maple Grove, MN (US); Steven E. Scott, Excelsior, MN (US); Gerald E. Loeb, South Pasadena, CA (US)

(73) Assignee: SetPoint Medical Corporation, Valencia, CA (US)

( * ) Notice: Subject to any disclaimer, the term of this patent is extended or adjusted under 35 U.S.C. 154(b) by 0 days.

(21) Appl. No.: 14/931,711

(22) Filed: Nov. 3, 2015

(65) Prior Publication Data

US 2016/0051813 A1 Feb. 25, 2016

Related U.S. Application Data

(60) Continuation of application No. 14/536,461, filed on Nov. 7, 2014, now Pat. No. 9,174,041, which is a
(Continued)

(51) Int. Cl.
*A61N 1/05* (2006.01)
*A61N 1/36* (2006.01)
(Continued)

(52) U.S. Cl.
CPC .......... *A61N 1/0556* (2013.01); *A61N 1/0558* (2013.01); *A61N 1/36114* (2013.01);
(Continued)

(58) Field of Classification Search
CPC .............. A61N 1/0556; A61N 1/37205; A61N 1/36053; A61N 1/0551; A61N 1/05;
(Continued)

(56) References Cited

U.S. PATENT DOCUMENTS 2,164,121 A 6/1939 Pescador
3,363,623 A 1/1968 Atwell
(Continued)

FOREIGN PATENT DOCUMENTS

CN 201230913 5/2009
CN 101528303 A 9/2009
(Continued)

OTHER PUBLICATIONS

US 6,184,239, 02/2001, Puskas (withdrawn)
(Continued)

*Primary Examiner* — Deborah Malamud
(74) *Attorney, Agent, or Firm* — Shay Glenn LLP

(57) ABSTRACT

An extravascular nerve cuff that is configured to hold a leadless, integral, implantable microstimulator. The nerve cuff may include a cuff body having a pocket or pouch for removably receiving the implantable device within. The nerve cuff can be secured around the nerve such that the electrodes of the device are stably positioned relative to the nerve. Furthermore, the nerve cuff drives the majority of the current from the stimulation device into the nerve, while shielding surrounding tissues from unwanted stimulation.

18 Claims, 18 Drawing Sheets

Related U.S. Application Data division of application No. 12/797,452, filed on Jun. 9, 2010, now Pat. No. 8,886,339.

(60) Provisional application No. 61/185,494, filed on Jun. 9, 2009.

(51) Int. Cl.
  *A61N 1/372* (2006.01)
  *A61N 1/375* (2006.01)

(52) U.S. Cl.
  CPC ............ *A61N 1/375* (2013.01); *A61N 1/3756* (2013.01); *A61N 1/37205* (2013.01)

(58) Field of Classification Search
  CPC ........ A61N 1/08; A61N 1/3606; A61N 1/375; A61N 1/3756; A61N 1/36125; A61N 1/0558; A61N 1/372
  See application file for complete search history.

(56) References Cited

U.S. PATENT DOCUMENTS

| | | |
|---|---|---|
| 3,631,534 A | 12/1971 | Hirota et al. |
| 4,073,296 A | 2/1978 | McCall |
| 4,098,277 A | 7/1978 | Mendell |
| 4,305,402 A | 12/1981 | Katims |
| 4,503,863 A | 3/1985 | Katims |
| 4,573,481 A | 3/1986 | Bullara |
| 4,590,946 A | 5/1986 | Loeb |
| 4,632,095 A | 12/1986 | Libin |
| 4,649,936 A | 3/1987 | Ungar et al. |
| 4,702,254 A | 10/1987 | Zabara |
| 4,840,793 A | 6/1989 | Todd, III et al. |
| 4,867,164 A | 9/1989 | Zabara |
| 4,929,734 A | 5/1990 | Coughenour et al. |
| 4,930,516 A | 6/1990 | Alfano et al. |
| 4,935,234 A | 6/1990 | Todd, III et al. |
| 4,979,511 A | 12/1990 | Terry, Jr. |
| 4,991,578 A | 2/1991 | Cohen |
| 5,019,648 A | 5/1991 | Schlossman et al. |
| 5,025,807 A | 6/1991 | Zabara |
| 5,038,781 A | 8/1991 | Lynch |
| 5,049,659 A | 9/1991 | Cantor et al. |
| 5,073,560 A | 12/1991 | Wu et al. |
| 5,106,853 A | 4/1992 | Showell et al. |
| 5,111,815 A | 5/1992 | Mower |
| 5,154,172 A | 10/1992 | Terry, Jr. et al. |
| 5,175,166 A | 12/1992 | Dunbar et al. |
| 5,179,950 A | 1/1993 | Stanislaw |
| 5,186,170 A | 2/1993 | Varrichio et al. |
| 5,188,104 A | 2/1993 | Wernicke et al. |
| 5,203,326 A | 4/1993 | Collins |
| 5,205,285 A | 4/1993 | Baker, Jr. |
| 5,215,086 A | 6/1993 | Terry, Jr. et al. |
| 5,215,089 A | 6/1993 | Baker, Jr. |
| 5,222,494 A | 6/1993 | Baker, Jr. |
| 5,231,988 A | 8/1993 | Wernicke et al. |
| 5,235,980 A | 8/1993 | Varrichio et al. |
| 5,237,991 A | 8/1993 | Baker et al. |
| 5,251,634 A | 10/1993 | Weinberg |
| 5,263,480 A | 11/1993 | Wernicke et al. |
| 5,269,303 A | 12/1993 | Wernicke et al. |
| 5,299,569 A | 4/1994 | Wernicke et al. |
| 5,304,206 A | 4/1994 | Baker, Jr. et al. |
| 5,330,507 A | 7/1994 | Schwartz |
| 5,330,515 A | 7/1994 | Rutecki et al. |
| 5,335,657 A | 8/1994 | Terry, Jr. et al. |
| 5,344,438 A | 9/1994 | Testerman et al. |
| 5,351,394 A | 10/1994 | Weinberg |
| 5,403,845 A | 4/1995 | Dunbar et al. |
| 5,458,625 A | 10/1995 | Kendall |
| 5,472,841 A | 12/1995 | Jayasena et al. |
| 5,487,756 A | 1/1996 | Kallesoe et al. |
| 5,496,938 A | 3/1996 | Gold et al. |
| 5,503,978 A | 4/1996 | Schneider et al. |
| 5,531,778 A | 7/1996 | Maschino et al. |
| 5,540,730 A | 7/1996 | Terry, Jr. et al. |
| 5,540,734 A | 7/1996 | Zabara |
| 5,567,588 A | 10/1996 | Gold et al. |
| 5,567,724 A | 10/1996 | Kelleher et al. |
| 5,571,150 A | 11/1996 | Wernicke et al. |
| 5,580,737 A | 12/1996 | Polisky et al. |
| 5,582,981 A | 12/1996 | Toole et al. |
| 5,604,231 A | 2/1997 | Smith et al. |
| 5,607,459 A | 3/1997 | Paul et al. |
| 5,611,350 A | 3/1997 | John |
| 5,618,818 A | 4/1997 | Ojo et al. |
| 5,629,285 A | 5/1997 | Black et al. |
| 5,637,459 A | 6/1997 | Burke et al. |
| 5,651,378 A | 7/1997 | Matheny et al. |
| 5,654,151 A | 8/1997 | Allen et al. |
| 5,683,867 A | 11/1997 | Biesecker et al. |
| 5,690,681 A | 11/1997 | Geddes et al. |
| 5,700,282 A | 12/1997 | Zabara |
| 5,705,337 A | 1/1998 | Gold et al. |
| 5,707,400 A | 1/1998 | Terry, Jr. et al. |
| 5,709,853 A | 1/1998 | Iino et al. |
| 5,712,375 A | 1/1998 | Jensen et al. |
| 5,718,912 A | 2/1998 | Thompson et al. |
| 5,726,017 A | 3/1998 | Lochrie et al. |
| 5,726,179 A | 3/1998 | Messer, Jr. et al. |
| 5,727,556 A | 3/1998 | Weth et al. |
| 5,733,255 A | 3/1998 | Dinh et al. |
| 5,741,802 A | 4/1998 | Kem et al. |
| 5,773,598 A | 6/1998 | Burke et al. |
| 5,786,462 A | 7/1998 | Schneider et al. |
| 5,788,656 A | 8/1998 | Mino |
| 5,792,210 A | 8/1998 | Wamubu et al. |
| 5,853,005 A | 12/1998 | Scanlon |
| 5,854,289 A | 12/1998 | Bianchi et al. |
| 5,902,814 A | 5/1999 | Gordon et al. |
| 5,913,876 A | 6/1999 | Taylor et al. |
| 5,916,239 A | 6/1999 | Geddes et al. |
| 5,919,216 A | 7/1999 | Houben et al. |
| 5,928,272 A | 7/1999 | Adkins et al. |
| 5,964,794 A | 10/1999 | Bolz et al. |
| 5,977,144 A | 11/1999 | Meyer et al. |
| 5,994,330 A | 11/1999 | El Khoury |
| 6,002,964 A | 12/1999 | Feler et al. |
| 6,006,134 A | 12/1999 | Hill et al. |
| 6,017,891 A | 1/2000 | Eibl et al. |
| 6,028,186 A | 2/2000 | Tasset et al. |
| 6,051,017 A | 4/2000 | Loeb et al. |
| 6,083,696 A | 7/2000 | Biesecker et al. |
| 6,083,905 A | 7/2000 | Voorberg et al. |
| 6,096,728 A | 8/2000 | Collins et al. |
| 6,104,956 A | 8/2000 | Naritoku et al. |
| 6,110,900 A | 8/2000 | Gold et al. |
| 6,110,914 A | 8/2000 | Phillips et al. |
| 6,117,837 A | 9/2000 | Tracey et al. |
| 6,124,449 A | 9/2000 | Gold et al. |
| 6,127,119 A | 10/2000 | Stephens et al. |
| 6,140,490 A | 10/2000 | Biesecker et al. |
| 6,141,590 A | 10/2000 | Renirie et al. |
| 6,147,204 A | 11/2000 | Gold et al. |
| 6,159,145 A | 12/2000 | Satoh |
| 6,164,284 A | 12/2000 | Schulman et al. |
| 6,166,048 A | 12/2000 | Bencherif |
| 6,168,778 B1 | 1/2001 | Janjic et al. |
| 6,171,795 B1 | 1/2001 | Korman et al. |
| 6,205,359 B1 | 3/2001 | Boveja |
| 6,208,894 B1 | 3/2001 | Schulman et al. |
| 6,208,902 B1 | 3/2001 | Boveja |
| 6,210,321 B1 | 4/2001 | Di Mino et al. |
| 6,224,862 B1 | 5/2001 | Turecek et al. |
| 6,233,488 B1 | 5/2001 | Hess |
| 6,266,564 B1 | 7/2001 | Hill et al. |
| 6,269,270 B1 | 7/2001 | Boveja |
| 6,304,775 B1 | 10/2001 | Iasemidis et al. |
| 6,308,104 B1 | 10/2001 | Taylor et al. |
| 6,337,997 B1 | 1/2002 | Rise |
| 6,339,725 B1 | 1/2002 | Naritoku et al. |
| 6,341,236 B1 | 1/2002 | Osorio et al. |

(56) References Cited

U.S. PATENT DOCUMENTS

| | | |
|---|---|---|
| 6,356,787 B1 | 3/2002 | Rezai et al. |
| 6,356,788 B2 | 3/2002 | Boveja |
| 6,381,499 B1 | 4/2002 | Taylor et al. |
| 6,405,732 B1 | 6/2002 | Edwards et al. |
| 6,407,095 B1 | 6/2002 | Lochead et al. |
| 6,428,484 B1 | 8/2002 | Battmer et al. |
| 6,429,217 B1 | 8/2002 | Puskas |
| 6,447,443 B1 | 9/2002 | Keogh et al. |
| 6,449,507 B1 | 9/2002 | Hill et al. |
| 6,473,644 B1 | 10/2002 | Terry, Jr. et al. |
| 6,479,523 B1 | 11/2002 | Puskas |
| 6,487,446 B1 | 11/2002 | Hill et al. |
| 6,511,500 B1 | 1/2003 | Rahme |
| 6,528,529 B1 | 3/2003 | Brann et al. |
| 6,532,388 B1 | 3/2003 | Hill et al. |
| 6,542,774 B2 | 4/2003 | Hill et al. |
| 6,556,868 B2 | 4/2003 | Naritoku et al. |
| 6,564,102 B1 | 5/2003 | Boveja |
| 6,587,719 B1 | 7/2003 | Barrett et al. |
| 6,587,727 B2 | 7/2003 | Osorio et al. |
| 6,600,956 B2 | 7/2003 | Maschino et al. |
| 6,602,891 B2 | 8/2003 | Messer et al. |
| 6,609,025 B2 | 8/2003 | Barrett et al. |
| 6,610,713 B2 | 8/2003 | Tracey |
| 6,611,715 B1 | 8/2003 | Boveja |
| 6,615,081 B1 | 9/2003 | Boveja |
| 6,615,085 B1 | 9/2003 | Boveja |
| 6,622,038 B2 | 9/2003 | Barrett et al. |
| 6,622,041 B2 | 9/2003 | Terry, Jr. et al. |
| 6,622,047 B2 | 9/2003 | Barrett et al. |
| 6,628,987 B1 | 9/2003 | Hill et al. |
| 6,633,779 B1 | 10/2003 | Schuler et al. |
| 6,656,960 B2 | 12/2003 | Puskas |
| 6,668,191 B1 | 12/2003 | Boveja |
| 6,671,556 B2 | 12/2003 | Osorio et al. |
| 6,684,105 B2 | 1/2004 | Cohen et al. |
| 6,690,973 B2 | 2/2004 | Hill et al. |
| 6,718,208 B2 | 4/2004 | Hill et al. |
| 6,721,603 B2 | 4/2004 | Zabara et al. |
| 6,735,471 B2 | 5/2004 | Hill et al. |
| 6,735,475 B1 | 5/2004 | Whitehurst et al. |
| 6,760,626 B1 | 7/2004 | Boveja |
| 6,778,854 B2 | 8/2004 | Puskas |
| 6,804,558 B2 | 10/2004 | Haller et al. |
| RE38,654 E | 11/2004 | Hill et al. |
| 6,826,428 B1 | 11/2004 | Chen et al. |
| 6,832,114 B1 | 12/2004 | Whitehurst et al. |
| 6,838,471 B2 | 1/2005 | Tracey |
| RE38,705 E | 2/2005 | Hill et al. |
| 6,879,859 B1 | 4/2005 | Boveja |
| 6,885,888 B2 | 4/2005 | Rezai |
| 6,901,294 B1 | 5/2005 | Whitehurst et al. |
| 6,904,318 B2 | 6/2005 | Hill et al. |
| 6,920,357 B2 | 7/2005 | Osorio et al. |
| 6,928,320 B2 | 8/2005 | King |
| 6,934,583 B2 | 8/2005 | Weinberg et al. |
| 6,937,903 B2 | 8/2005 | Schuler et al. |
| 6,961,618 B2 | 11/2005 | Osorio et al. |
| 6,978,787 B2 | 12/2005 | Broniatowski |
| 7,011,638 B2 | 3/2006 | Schuler et al. |
| 7,054,686 B2 | 5/2006 | MacDonald |
| 7,054,692 B1 | 5/2006 | Whitehurst et al. |
| 7,058,447 B2 | 6/2006 | Hill et al. |
| 7,062,320 B2 | 6/2006 | Ehlinger, Jr. |
| 7,069,082 B2 | 6/2006 | Lindenthaler |
| 7,072,720 B2 | 7/2006 | Puskas |
| 7,076,307 B2 | 7/2006 | Boveja et al. |
| 7,142,910 B2 | 11/2006 | Puskas |
| 7,142,917 B2 | 11/2006 | Fukui |
| 7,149,574 B2 | 12/2006 | Yun et al. |
| 7,155,279 B2 | 12/2006 | Whitehurst et al. |
| 7,155,284 B1 | 12/2006 | Whitehurst et al. |
| 7,167,750 B2 | 1/2007 | Knudson et al. |
| 7,167,751 B1 | 1/2007 | Whitehurst et al. |
| 7,174,218 B1 | 2/2007 | Kuzma |
| 7,184,828 B2 | 2/2007 | Hill et al. |
| 7,184,829 B2 | 2/2007 | Hill et al. |
| 7,191,012 B2 | 3/2007 | Boveja et al. |
| 7,204,815 B2 | 4/2007 | Connor |
| 7,209,787 B2 | 4/2007 | DiLorenzo |
| 7,225,019 B2 | 5/2007 | Jahns et al. |
| 7,228,167 B2 | 6/2007 | Kara et al. |
| 7,238,715 B2 | 7/2007 | Tracey et al. |
| 7,242,984 B2 | 7/2007 | DiLorenzo |
| 7,269,457 B2 | 9/2007 | Shafer et al. |
| 7,345,178 B2 | 3/2008 | Nunes et al. |
| 7,467,016 B2 | 12/2008 | Colborn |
| 7,544,497 B2 | 6/2009 | Sinclair et al. |
| 7,561,918 B2 | 7/2009 | Armstrong et al. |
| 7,711,432 B2 | 5/2010 | Thimineur et al. |
| 7,729,760 B2 | 6/2010 | Patel et al. |
| 7,751,891 B2 | 7/2010 | Armstrong et al. |
| 7,776,326 B2 | 8/2010 | Milbrandt et al. |
| 7,797,058 B2 | 9/2010 | Mrva et al. |
| 7,819,883 B2 | 10/2010 | Westlund et al. |
| 7,822,486 B2 | 10/2010 | Foster et al. |
| 7,829,556 B2 | 11/2010 | Bemis et al. |
| 7,869,885 B2 | 1/2011 | Begnaud et al. |
| 7,937,145 B2 | 5/2011 | Dobak |
| 7,962,220 B2 | 6/2011 | Kolafa et al. |
| 7,974,701 B2 | 7/2011 | Armstrong |
| 7,974,707 B2 | 7/2011 | Inman |
| 7,996,088 B2 | 8/2011 | Marrosu et al. |
| 7,996,092 B2 | 8/2011 | Mrva et al. |
| 8,019,419 B1 | 9/2011 | Panescu et al. |
| 8,103,349 B2 | 1/2012 | Donders et al. |
| 8,165,668 B2 | 4/2012 | Dacey, Jr. et al. |
| 8,180,446 B2 | 5/2012 | Dacey, Jr. et al. |
| 8,195,287 B2 | 6/2012 | Dacey, Jr. et al. |
| 8,214,056 B2 | 7/2012 | Hoffer et al. |
| 8,233,982 B2 | 7/2012 | Libbus |
| 8,391,970 B2 | 3/2013 | Tracey et al. |
| 8,412,338 B2 | 4/2013 | Faltys |
| 8,612,002 B2 | 12/2013 | Faltys et al. |
| 8,729,129 B2 | 5/2014 | Tracey et al. |
| 8,788,034 B2 | 7/2014 | Levine et al. |
| 8,843,210 B2 | 9/2014 | Simon et al. |
| 8,855,767 B2 | 10/2014 | Faltys et al. |
| 8,886,339 B2 | 11/2014 | Faltys et al. |
| 8,914,114 B2 | 12/2014 | Tracey et al. |
| 8,918,178 B2 | 12/2014 | Simon et al. |
| 8,983,628 B2 | 3/2015 | Simon et al. |
| 8,983,629 B2 | 3/2015 | Simon et al. |
| 8,996,116 B2 | 3/2015 | Faltys et al. |
| 9,162,064 B2 | 10/2015 | Faltys et al. |
| 9,174,041 B2 | 11/2015 | Faltys et al. |
| 9,211,409 B2 | 12/2015 | Tracey et al. |
| 9,211,410 B2 | 12/2015 | Levine et al. |
| 9,254,383 B2 | 2/2016 | Simon et al. |
| 9,403,001 B2 | 8/2016 | Simon et al. |
| 2001/0002441 A1 | 5/2001 | Boveja |
| 2002/0026141 A1 | 2/2002 | Houben et al. |
| 2002/0040035 A1 | 4/2002 | Myers et al. |
| 2002/0077675 A1 | 6/2002 | Greenstein |
| 2002/0086871 A1 | 7/2002 | O'Neill et al. |
| 2002/0095139 A1 | 7/2002 | Keogh et al. |
| 2002/0099417 A1 | 7/2002 | Naritoku et al. |
| 2002/0138075 A1 | 9/2002 | Edwards et al. |
| 2002/0138109 A1 | 9/2002 | Keogh et al. |
| 2002/0193859 A1 | 12/2002 | Schulman et al. |
| 2002/0198570 A1 | 12/2002 | Puskas |
| 2003/0018367 A1 | 1/2003 | DiLorenzo |
| 2003/0045909 A1 | 3/2003 | Gross et al. |
| 2003/0088301 A1 | 5/2003 | King |
| 2003/0191404 A1 | 10/2003 | Klein |
| 2003/0194752 A1 | 10/2003 | Anderson et al. |
| 2003/0195578 A1 | 10/2003 | Perron et al. |
| 2003/0212440 A1 | 11/2003 | Boveja |
| 2003/0229380 A1 | 12/2003 | Adams et al. |
| 2003/0236557 A1 | 12/2003 | Whitehurst et al. |
| 2003/0236558 A1 | 12/2003 | Whitehurst et al. |
| 2004/0015202 A1 | 1/2004 | Chandler et al. |
| 2004/0015205 A1 | 1/2004 | Whitehurst et al. |
| 2004/0024422 A1 | 2/2004 | Hill et al. |

(56) References Cited

U.S. PATENT DOCUMENTS

| | | |
|---|---|---|
| 2004/0024428 A1 | 2/2004 | Barrett et al. |
| 2004/0024439 A1 | 2/2004 | Riso |
| 2004/0030362 A1 | 2/2004 | Hill et al. |
| 2004/0039427 A1 | 2/2004 | Barrett et al. |
| 2004/0048795 A1 | 3/2004 | Ivanova et al. |
| 2004/0049121 A1 | 3/2004 | Yaron |
| 2004/0049240 A1 | 3/2004 | Gerber et al. |
| 2004/0059383 A1 | 3/2004 | Puskas |
| 2004/0111139 A1 | 6/2004 | McCreery et al. |
| 2004/0138517 A1 | 7/2004 | Osorio et al. |
| 2004/0138518 A1 | 7/2004 | Rise et al. |
| 2004/0138536 A1 | 7/2004 | Frei et al. |
| 2004/0146949 A1 | 7/2004 | Tan et al. |
| 2004/0153127 A1 | 8/2004 | Gordon et al. |
| 2004/0158119 A1 | 8/2004 | Osorio et al. |
| 2004/0162584 A1 | 8/2004 | Hill et al. |
| 2004/0172074 A1 | 9/2004 | Yoshihito |
| 2004/0172085 A1 | 9/2004 | Knudson et al. |
| 2004/0172086 A1 | 9/2004 | Knudson et al. |
| 2004/0172088 A1 | 9/2004 | Knudson et al. |
| 2004/0172094 A1 | 9/2004 | Cohen et al. |
| 2004/0176812 A1 | 9/2004 | Knudson et al. |
| 2004/0178706 A1 | 9/2004 | D'Orso |
| 2004/0193231 A1 | 9/2004 | David et al. |
| 2004/0199209 A1 | 10/2004 | Hill et al. |
| 2004/0199210 A1 | 10/2004 | Shelchuk |
| 2004/0204355 A1 | 10/2004 | Tracey et al. |
| 2004/0215287 A1 | 10/2004 | Swoyer et al. |
| 2004/0236381 A1 | 11/2004 | Dinsmoor et al. |
| 2004/0236382 A1 | 11/2004 | Dinsmoor et al. |
| 2004/0240691 A1 | 12/2004 | Grafenberg |
| 2004/0243182 A1 | 12/2004 | Cohen et al. |
| 2004/0254612 A1 | 12/2004 | Ezra et al. |
| 2004/0267152 A1 | 12/2004 | Pineda |
| 2005/0021092 A1 | 1/2005 | Yun et al. |
| 2005/0021101 A1 | 1/2005 | Chen et al. |
| 2005/0027328 A1 | 2/2005 | Greenstein |
| 2005/0043774 A1 | 2/2005 | Devlin et al. |
| 2005/0049655 A1 | 3/2005 | Boveja et al. |
| 2005/0065553 A1 | 3/2005 | Ben Ezra et al. |
| 2005/0065573 A1 | 3/2005 | Rezai |
| 2005/0065575 A1 | 3/2005 | Dobak |
| 2005/0070970 A1 | 3/2005 | Knudson et al. |
| 2005/0070974 A1 | 3/2005 | Knudson et al. |
| 2005/0075701 A1 | 4/2005 | Shafer |
| 2005/0075702 A1 | 4/2005 | Shafer |
| 2005/0095246 A1 | 5/2005 | Shafer |
| 2005/0096707 A1 | 5/2005 | Hill et al. |
| 2005/0131467 A1 | 6/2005 | Boveja |
| 2005/0131486 A1 | 6/2005 | Boveja et al. |
| 2005/0131487 A1 | 6/2005 | Boveja |
| 2005/0131493 A1 | 6/2005 | Boveja et al. |
| 2005/0137644 A1 | 6/2005 | Boveja et al. |
| 2005/0137645 A1 | 6/2005 | Voipio et al. |
| 2005/0143781 A1 | 6/2005 | Carbunaru et al. |
| 2005/0143787 A1 | 6/2005 | Boveja et al. |
| 2005/0149126 A1 | 7/2005 | Libbus |
| 2005/0149129 A1 | 7/2005 | Libbus et al. |
| 2005/0149131 A1 | 7/2005 | Libbus et al. |
| 2005/0153885 A1 | 7/2005 | Yun et al. |
| 2005/0154425 A1 | 7/2005 | Boveja et al. |
| 2005/0154426 A1 | 7/2005 | Boveja et al. |
| 2005/0165458 A1 | 7/2005 | Boveja et al. |
| 2005/0177200 A1 | 8/2005 | George et al. |
| 2005/0182288 A1 | 8/2005 | Zabara |
| 2005/0182467 A1 | 8/2005 | Hunter et al. |
| 2005/0187584 A1 | 8/2005 | Denker et al. |
| 2005/0187586 A1 | 8/2005 | David et al. |
| 2005/0187590 A1 | 8/2005 | Boveja et al. |
| 2005/0192644 A1 | 9/2005 | Boveja et al. |
| 2005/0197600 A1 | 9/2005 | Schuler et al. |
| 2005/0197675 A1 | 9/2005 | David et al. |
| 2005/0197678 A1 | 9/2005 | Boveja et al. |
| 2005/0203501 A1 | 9/2005 | Aldrich et al. |
| 2005/0209654 A1 | 9/2005 | Boveja et al. |
| 2005/0216064 A1 | 9/2005 | Heruth et al. |
| 2005/0216070 A1 | 9/2005 | Boveja et al. |
| 2005/0216071 A1 | 9/2005 | Devlin et al. |
| 2005/0240229 A1 | 10/2005 | Whitehurst et al. |
| 2005/0240231 A1 | 10/2005 | Aldrich et al. |
| 2005/0240241 A1 | 10/2005 | Yun et al. |
| 2005/0240242 A1 | 10/2005 | DiLorenzo |
| 2005/0251220 A1 | 11/2005 | Barrett et al. |
| 2005/0251222 A1 | 11/2005 | Barrett et al. |
| 2005/0267542 A1 | 12/2005 | David et al. |
| 2005/0267547 A1 | 12/2005 | Knudson et al. |
| 2005/0283198 A1 | 12/2005 | Haubrich et al. |
| 2006/0009815 A1 | 1/2006 | Boveja et al. |
| 2006/0015151 A1 | 1/2006 | Aldrich |
| 2006/0025828 A1 | 2/2006 | Armstrong et al. |
| 2006/0036293 A1 | 2/2006 | Whitehurst et al. |
| 2006/0052657 A9 | 3/2006 | Zabara |
| 2006/0052831 A1 | 3/2006 | Fukui |
| 2006/0052836 A1 | 3/2006 | Kim et al. |
| 2006/0058851 A1 | 3/2006 | Cigaina |
| 2006/0064137 A1 | 3/2006 | Stone |
| 2006/0064139 A1 | 3/2006 | Chung et al. |
| 2006/0074450 A1 | 4/2006 | Boveja et al. |
| 2006/0074473 A1 | 4/2006 | Gertner |
| 2006/0079936 A1 | 4/2006 | Boveja et al. |
| 2006/0085046 A1 | 4/2006 | Rezai et al. |
| 2006/0095081 A1 | 5/2006 | Zhou et al. |
| 2006/0095090 A1 | 5/2006 | De Ridder |
| 2006/0100668 A1 | 5/2006 | Ben-David et al. |
| 2006/0106755 A1 | 5/2006 | Stuhec |
| 2006/0111644 A1 | 5/2006 | Guttag et al. |
| 2006/0111754 A1 | 5/2006 | Rezai et al. |
| 2006/0111755 A1 | 5/2006 | Stone et al. |
| 2006/0116739 A1 | 6/2006 | Betser et al. |
| 2006/0122675 A1 | 6/2006 | Libbus et al. |
| 2006/0129200 A1 | 6/2006 | Kurokawa |
| 2006/0129202 A1 | 6/2006 | Armstrong |
| 2006/0135998 A1 | 6/2006 | Libbus et al. |
| 2006/0142802 A1 | 6/2006 | Armstrong |
| 2006/0142822 A1 | 6/2006 | Tulgar |
| 2006/0149337 A1 | 7/2006 | John |
| 2006/0161216 A1 | 7/2006 | John et al. |
| 2006/0161217 A1 | 7/2006 | Jaax et al. |
| 2006/0167497 A1 | 7/2006 | Armstrong et al. |
| 2006/0167498 A1 | 7/2006 | DiLorenzo |
| 2006/0167501 A1 | 7/2006 | Ben-David et al. |
| 2006/0173493 A1 | 8/2006 | Armstrong et al. |
| 2006/0173508 A1 | 8/2006 | Stone et al. |
| 2006/0178691 A1 | 8/2006 | Binmoeller |
| 2006/0178703 A1 | 8/2006 | Huston et al. |
| 2006/0178706 A1 | 8/2006 | Lisogurski et al. |
| 2006/0190044 A1 | 8/2006 | Libbus et al. |
| 2006/0200208 A1 | 9/2006 | Terry, Jr. et al. |
| 2006/0200219 A1 | 9/2006 | Thrope et al. |
| 2006/0206155 A1 | 9/2006 | Ben-David et al. |
| 2006/0206158 A1 | 9/2006 | Wu et al. |
| 2006/0229677 A1 | 10/2006 | Moffitt et al. |
| 2006/0229681 A1 | 10/2006 | Fischell |
| 2006/0241699 A1 | 10/2006 | Libbus et al. |
| 2006/0247719 A1 | 11/2006 | Maschino et al. |
| 2006/0247721 A1 | 11/2006 | Maschino et al. |
| 2006/0247722 A1 | 11/2006 | Maschino et al. |
| 2006/0259077 A1 | 11/2006 | Pardo et al. |
| 2006/0259084 A1 | 11/2006 | Zhang et al. |
| 2006/0259085 A1 | 11/2006 | Zhang et al. |
| 2006/0259107 A1 | 11/2006 | Caparso et al. |
| 2006/0271115 A1 | 11/2006 | Ben-Ezra et al. |
| 2006/0282121 A1 | 12/2006 | Payne et al. |
| 2006/0282131 A1 | 12/2006 | Caparso et al. |
| 2006/0282145 A1 | 12/2006 | Caparso et al. |
| 2006/0287678 A1 | 12/2006 | Shafer |
| 2006/0287679 A1 | 12/2006 | Stone |
| 2006/0292099 A1 | 12/2006 | Milburn et al. |
| 2006/0293720 A1 | 12/2006 | DiLorenzo |
| 2006/0293721 A1 | 12/2006 | Tarver et al. |
| 2006/0293723 A1 | 12/2006 | Whitehurst et al. |
| 2007/0016262 A1 | 1/2007 | Gross et al. |
| 2007/0016263 A1 | 1/2007 | Armstrong et al. |
| 2007/0021785 A1 | 1/2007 | Inman et al. |

(56) References Cited

U.S. PATENT DOCUMENTS

| | | |
|---|---|---|
| 2007/0021786 A1 | 1/2007 | Parnis et al. |
| 2007/0021814 A1 | 1/2007 | Inman et al. |
| 2007/0025608 A1 | 2/2007 | Armstrong |
| 2007/0027482 A1 | 2/2007 | Parnis et al. |
| 2007/0027483 A1 | 2/2007 | Maschino et al. |
| 2007/0027484 A1 | 2/2007 | Guzman et al. |
| 2007/0027486 A1 | 2/2007 | Armstrong |
| 2007/0027492 A1 | 2/2007 | Maschino et al. |
| 2007/0027496 A1 | 2/2007 | Parnis et al. |
| 2007/0027497 A1 | 2/2007 | Parnis |
| 2007/0027498 A1 | 2/2007 | Maschino et al. |
| 2007/0027499 A1 | 2/2007 | Maschino et al. |
| 2007/0027500 A1 | 2/2007 | Maschino et al. |
| 2007/0027504 A1 | 2/2007 | Barrett et al. |
| 2007/0055324 A1 | 3/2007 | Thompson et al. |
| 2007/0067004 A1 | 3/2007 | Boveja et al. |
| 2007/0083242 A1 | 4/2007 | Mazgalev et al. |
| 2007/0093434 A1 | 4/2007 | Rossetti et al. |
| 2007/0093870 A1 | 4/2007 | Maschino |
| 2007/0093875 A1 | 4/2007 | Chavan et al. |
| 2007/0100263 A1 | 5/2007 | Merfeld |
| 2007/0100377 A1 | 5/2007 | Armstrong et al. |
| 2007/0100378 A1 | 5/2007 | Maschino |
| 2007/0100380 A1 | 5/2007 | Fukui |
| 2007/0100392 A1 | 5/2007 | Maschino et al. |
| 2007/0106339 A1 | 5/2007 | Errico et al. |
| 2007/0112404 A1 | 5/2007 | Mann et al. |
| 2007/0118177 A1 | 5/2007 | Libbus et al. |
| 2007/0118178 A1 | 5/2007 | Fukui |
| 2007/0129767 A1 | 6/2007 | Wahlstrand |
| 2007/0129780 A1 | 6/2007 | Whitehurst et al. |
| 2007/0135846 A1 | 6/2007 | Knudson et al. |
| 2007/0135856 A1 | 6/2007 | Knudson et al. |
| 2007/0135857 A1 | 6/2007 | Knudson et al. |
| 2007/0135858 A1 | 6/2007 | Knudson et al. |
| 2007/0135870 A1 | 6/2007 | Knudson et al. |
| 2007/0142871 A1 | 6/2007 | Libbus et al. |
| 2007/0142874 A1 | 6/2007 | John |
| 2007/0150006 A1 | 6/2007 | Libbus et al. |
| 2007/0150011 A1 | 6/2007 | Meyer et al. |
| 2007/0150021 A1 | 6/2007 | Chen et al. |
| 2007/0150027 A1 | 6/2007 | Rogers |
| 2007/0156180 A1 | 7/2007 | Jaax et al. |
| 2007/0198063 A1 | 8/2007 | Hunter et al. |
| 2007/0239243 A1 | 10/2007 | Moffitt et al. |
| 2007/0244522 A1 | 10/2007 | Overstreet |
| 2007/0250145 A1 | 10/2007 | Kraus et al. |
| 2007/0255320 A1 | 11/2007 | Inman et al. |
| 2007/0255333 A1 | 11/2007 | Giftakis |
| 2007/0255339 A1 | 11/2007 | Torgerson |
| 2008/0021517 A1 | 1/2008 | Dietrich |
| 2008/0021520 A1 | 1/2008 | Dietrich |
| 2008/0046055 A1 | 2/2008 | Durand et al. |
| 2008/0058871 A1 | 3/2008 | Libbus et al. |
| 2008/0103407 A1 | 5/2008 | Bolea et al. |
| 2008/0140138 A1 | 6/2008 | Ivanova et al. |
| 2008/0183226 A1 | 7/2008 | Buras et al. |
| 2008/0183246 A1 | 7/2008 | Patel et al. |
| 2008/0195171 A1 | 8/2008 | Sharma |
| 2008/0208266 A1 | 8/2008 | Lesser et al. |
| 2008/0234790 A1 | 9/2008 | Bayer et al. |
| 2008/0249439 A1 | 10/2008 | Tracey et al. |
| 2008/0281365 A1 | 11/2008 | Tweden et al. |
| 2008/0281372 A1 | 11/2008 | Libbus et al. |
| 2009/0012590 A1 | 1/2009 | Inman et al. |
| 2009/0048194 A1 | 2/2009 | Aerssens et al. |
| 2009/0082832 A1 | 3/2009 | Carbunaru et al. |
| 2009/0105782 A1 | 4/2009 | Mickle et al. |
| 2009/0123521 A1 | 5/2009 | Weber et al. |
| 2009/0125079 A1 | 5/2009 | Armstrong et al. |
| 2009/0143831 A1 | 6/2009 | Huston et al. |
| 2009/0171405 A1 | 7/2009 | Craig |
| 2009/0177112 A1 | 7/2009 | Gharib et al. |
| 2009/0187231 A1 | 7/2009 | Errico et al. |
| 2009/0248097 A1 | 10/2009 | Tracey et al. |
| 2009/0254143 A1 | 10/2009 | Tweden et al. |
| 2009/0275997 A1 | 11/2009 | Faltys et al. |
| 2009/0276019 A1 | 11/2009 | Perez et al. |
| 2009/0281593 A9 | 11/2009 | Errico et al. |
| 2010/0003656 A1 | 1/2010 | Kilgard et al. |
| 2010/0010603 A1 | 1/2010 | Ben-David et al. |
| 2010/0042186 A1 | 2/2010 | Ben-David et al. |
| 2010/0063563 A1 | 3/2010 | Craig |
| 2010/0074934 A1 | 3/2010 | Hunter |
| 2010/0191304 A1 | 7/2010 | Scott |
| 2010/0215632 A1 | 8/2010 | Boss et al. |
| 2010/0241183 A1 | 9/2010 | DiLorenzo |
| 2010/0249859 A1 | 9/2010 | DiLorenzo |
| 2010/0280562 A1 | 11/2010 | Pi et al. |
| 2010/0280569 A1 | 11/2010 | Bobillier et al. |
| 2011/0004266 A1 | 1/2011 | Sharma |
| 2011/0054569 A1 | 3/2011 | Zitnik et al. |
| 2011/0066208 A1 | 3/2011 | Pasricha et al. |
| 2011/0082515 A1 | 4/2011 | Libbus et al. |
| 2011/0092882 A1 | 4/2011 | Firlik et al. |
| 2011/0144717 A1 | 6/2011 | Burton et al. |
| 2011/0224749 A1 | 9/2011 | Ben-David et al. |
| 2011/0307027 A1 | 12/2011 | Sharma et al. |
| 2012/0065706 A1 | 3/2012 | Vallapureddy et al. |
| 2012/0185020 A1 | 7/2012 | Simon et al. |
| 2013/0066392 A1 | 3/2013 | Simon et al. |
| 2013/0066395 A1 | 3/2013 | Simon et al. |
| 2013/0079834 A1 | 3/2013 | Levine |
| 2013/0253413 A1 | 9/2013 | Levine et al. |
| 2013/0317580 A1 | 11/2013 | Simon et al. |
| 2015/0100100 A1 | 4/2015 | Tracey et al. |
| 2015/0241447 A1 | 8/2015 | Zitnik et al. |
| 2016/0096016 A1 | 4/2016 | Tracey et al. |
| 2016/0096017 A1 | 4/2016 | Levine et al. |
| 2016/0367808 A9 | 12/2016 | Simon et al. |

FOREIGN PATENT DOCUMENTS

| | | |
|---|---|---|
| CN | 101578067 A | 11/2009 |
| CN | 101868280 A | 10/2010 |
| DE | 2628045 A1 | 1/1977 |
| DE | 3736664 A1 | 5/1989 |
| DE | 20316509 U1 | 4/2004 |
| EP | 0438510 B1 | 8/1996 |
| EP | 0726791 B1 | 6/2000 |
| EP | 1001827 B1 | 1/2004 |
| EP | 2213330 A2 | 8/2010 |
| EP | 2073896 B1 | 10/2011 |
| GB | 04133 | 2/1910 |
| WO | WO93/01862 A1 | 2/1993 |
| WO | WO97/30998 A1 | 8/1997 |
| WO | WO98/20868 A1 | 5/1998 |
| WO | WO00/27381 A2 | 5/2000 |
| WO | WO00/47104 A2 | 8/2000 |
| WO | WO01/00273 A1 | 1/2001 |
| WO | WO01/08617 A1 | 2/2001 |
| WO | WO01/89526 A1 | 11/2001 |
| WO | WO02/44176 A1 | 6/2002 |
| WO | WO02/057275 A1 | 7/2002 |
| WO | WO03/072135 A2 | 9/2003 |
| WO | WO04/000413 A2 | 12/2003 |
| WO | WO2004/064918 A1 | 8/2004 |
| WO | WO2006/073484 A1 | 7/2006 |
| WO | WO2006/076681 A2 | 7/2006 |
| WO | WO2007/133718 A2 | 11/2007 |
| WO | WO2010/005482 A1 | 1/2010 |
| WO | WO2010/067360 A2 | 6/2010 |

OTHER PUBLICATIONS

Faltys et al.; U.S. Appl. No. 15/153,639 entitled "External programmer," filed May 12, 2016.

Abraham, Coagulation abnormalities in acute lung injury and sepsis, Am. J. Respir. Cell Mol. Biol., vol. 22(4), pp. 401-404, Apr. 2000.

Aekerlund et al., Anti-inflammatory effects of a new tumour necrosis factor-alpha (TNF-Alpha) inhibitor (CNI-1493) in collagen-

(56) References Cited

OTHER PUBLICATIONS induced arthritis (CIA) in rats, Clinical & Experimental Immunology, vol. 115, No. 1, pp. 32-41, Jan. 1, 1999.
Antonica, A., et al., Vagal control of lymphocyte release from rat thymus, J. Auton. Nerv. Syst., vol. 48(3), pp. 187-197, Aug. 1994.
Asakura et al., Non-surgical therapy for ulcerative colitis, Nippon Geka Gakkai Zasshi, vol. 98, No. 4, pp. 431-437, Apr. 1997 (abstract only).
Beliavskaia et al.,"On the effects of prolonged stimulation of the peripheral segment of the vagus nerve . . . ," Fiziologicheskii Zhurnal SSSR Imeni I.M. Sechenova., vol. 52(11); p. 1315-1321, Nov 1966.
Ben-Noun et al.; Neck circumference as a simple screening measure for identifying overweight and obese patients; Obesity Research; vol. 9; No. 8; pp. 470-477; Aug. 8, 2001.
Benoist, et al., "Mast cells in autoimmune disease" Nature., vol. 420(19): pp. 875-878, Dec. 2002.
Benthem et al.; Parasympathetic inhibition of sympathetic neural activity to the pancreas; Am.J.Physiol Endocrinol.Metab; 280(2); pp. E378-E381; Feb. 2001.
Bernik et al., Vagus nerve stimulation attenuates cardiac TNF production in endotoxic shock, (supplemental to Shock, vol. 15, 2001, Injury, inflammation and sepsis: laboratory and clinical approaches, Shock, Abstracts, 24th Annual Conference on Shock, Marco Island, FL, Jun. 9-12, 2001), Abstract No. 81.
Bernik et al., Vagus nerve stimulation attenuates endotoxic shock and cardiac TNF production, 87th Clinical Congress of the American College of Surgeons, New Orleans, LA, Oct. 9, 2001.
Bernik et al., Vagus nerve stimulation attenuates LPS—induced cardiac TNF production and myocardial depression IN shock, New York Surgical Society, New York, NY, Apr. 11, 2001.
Bernik, et al., Pharmacological stimulation of the cholinergic anti-inflammatory pathway, The Journal of Experimental Medicine, vol. 195, No. 6, pp. 781-788, Mar. 18, 2002.
Besedovsky, H., et al., Immunoregulatory feedback between interleukin-1 and glucocorticoid hormones, Science, vol. 233, No. 4764, pp. 652-654, Aug. 1986.
Bhattacharya, S.K. et al., Central muscarinic receptor subtypes and carrageenin-induced paw oedema in rats, Res. Esp. Med. vol. 191(1), pp. 65-76, Dec. 1991.
Bianchi et al., Suppression of proinflammatory cytokines in monocytes by a tetravalent guanylhydrazone, Journal of Experimental Medicine, vol. 183, pp. 927-936, Mar. 1996.
Biggio et al.; Chronic vagus nerve stimulation induces neuronal plasticity in the rat hippocampus; Int. J. Neurpsychopharmacol.; vol. 12; No. 9; pp. 1209-1221; Oct. 2009.
Blackwell, T. S. et al., Sepsis and cytokines: current status, Br. J. Anaesth., vol. 77(1), pp. 110-117, Jul. 1996.
Blum, A. et al., Role of cytokines in heart failure, Am. Heart J., vol. 135 (2), pp. 181-186, Feb. 1998.
Boldyreff, Gastric and intestinal mucus, its properties and physiological importance, Acta Medica Scandinavica (journal), vol. 89, Issue 1-2, pp. 1-14, Jan./Dec. 1936.
Borovikova et al., Acetylcholine inhibition of immune response to bacterial endotoxin in human macrophages, Abstracts, Society for Neuroscience, 29th Annual Meeting, Miami Beach, FL, (Abs. No. 624.6); Oct. 23-28, 1999.
Borovikova et al., Efferent vagus nerve activity attenuates cytokine-mediated inflammation, Society for Neuroscience Abstracts, vol. 26, No. 102, Nov. 4-9, 2000 (abstract only).
Borovikova et al., Intracerebroventricular CNI-1493 prevents LPS-induced hypotension and peak serum TNF at a four-log lower dose than systemic treatment, 21st Annual Conference on Shock, San Antonio, TX, Jun. 14-17, 1998, Abstract No. 86.
Borovikova et al., Role of the efferent vagus nerve signaling in the regulation of the innate immune response to LPS, (supplemental to Shock, vol. 13, 2000, Molecular, cellular, and systemic pathobiological aspects and therapeutic approaches, abstracts, 5th World Congress on Trauma, Shock inflammation and sepsis-pathophysiology, immune consequences and therapy, Feb. 29, 2000-Mar. 4, 2000, Munich, DE), Abstract No. 166.
Borovikova et al., Role of the vagus nerve in the anti-inflammatory effects of CNI-1493, the FASEB journal, vol. 14, No. 4, 2000 (Experimental Biology 2000, San Diego, CA, Apr. 15-18, 2000, Abstract No. 97.9).
Borovikova et al., Vagotomy blocks the protective effects of I.C.V. CNI-1493 against LPS-induced shock, (Supplemental to Shock, vol. 11, 1999, Molecular, cellular, and systemic pathobioligal aspects and therapeutic approaches, abstacts and program, Fourth International Shock Congress and 22nd Annual Conference on Shock, Philadelphia, PA, Jun. 12-16, 1999), Abstract No. 277.
Borovikova, L. V., et al., Role of vagus nerve signaling in CNI-1493-mediated suppression of acute inflammation, Autonomic Neuroscience, vol. 85, No. 1-3, pp. 141-147, Dec. 20, 2000.
Borovikova, L. V., et al., Vagus nerve stimulation attenuates the systemic inflammatory response to endotoxin, Nature, vol. 405, No. 6785: pp. 458-462, May 25, 2000.
Bulloch et al.; Characterization of choline O-acetyltransferase (ChAT) in the BALB/C mouse spleen; Int.J.Neurosci.; 76(1-2); pp. 141-149; May 1994.
Bumgardner, G. L. et al., Transplantation and cytokines, Seminars in Liver Disease, vol. 19, No. 2, pp. 189-204, (year of pub. Sufficiently earlier than effective US filed and any foreign priority date) 1999.
Burke et al., Bent pseudoknots and novel RNA inhibitors of type 1 human immunodeficiency virus (HIV-1) reverse transcriptase, J. Mol. Biol., vol. 264(4); pp. 650-666, Dec. 1996.
Bushby et al; Centiles for adult head circumference; Archives of Disease in Childhood; vol. 67(10); pp. 1286-1287; Oct. 1992.
Cano et al.; Characterization of the central nervous system innervation of the rat spleen using viral transneuronal tracing; J.Comp Neurol.; 439(1); pp. 1-18; Oct. 2001.
Carteron, N. L., Cytokines in rheumatoid arthritis: trials and tribulations, Mol. Med. Today, vol. 6(8), pp. 315-323, Aug. 2000.
Cicala et al., "Linkage between inflammation and coagulation: An update on the molecular basis of the crosstalk," Life Sciences, vol. 62(20); pp. 1817-1824, Apr. 1998.
Clark et al.; Enhanced recognition memory following vagus nerve stimulation in human subjects; Nat. Neurosci.; 2(1); pp. 94-98; Jan. 1999.
Cohen, "The immunopathogenesis of sepsis," Nature., vol. 420(6917): pp. 885-891, Dec. 2002.
Corcoran, et al., The effects of vagus nerve stimulation on pro- and anti-inflammatory cytokines in humans: a preliminary report, NeuroImmunoModulation, vol. 12(5), pp. 307-309, Sep. 2005.
DAS, Critical advances in spticemia and septic shock, Critical Care, vol. 4, pp. 290-296, Sep. 7, 2000.
Del Signore et al; Nicotinic acetylcholine receptor subtypes in the rat sympathetic ganglion: pharmacological characterization, subcellular distribution and effect of pre- and postganglionic nerve crush; J.Neuropathol.Exp.Neurol.; 63(2); pp. 138-150; Feb. 2004.
Dibbs, Z., et al., Cytokines in heart failure: pathogenetic mechanisms and potential treatment, Proc. Assoc. Am. Physicians, vol. 111, No. 5, pp. 423-428, Sep.-Oct. 1999.
Dinarello, C. A., The interleukin-1 family: 10 years of discovery, Faseb J., vol. 8, No. 15, pp. 1314-1325, Dec. 1994.
Dorr et al.; Effect of vagus nerve stimulation on serotonergic and noradrenergic transmission; J. Pharmacol. Exp. Ther.; 318(2); pp. 890-898; Aug. 2006.
Doshi et al., Evolving role of tissue factor and its pathway inhibitor, Crit. Care Med., vol. 30, suppl. 5, pp. S241-S250, May 2002.
Elenkov et al.; Stress, corticotropin-releasing hormone, glucocorticoids, and the immune / inflammatory response: acute and chronic effects; Ann. N.Y. Acad. Sci.; 876; pp. 1-13; Jun. 22, 1999.
Ellington et al., In vitro selection of RNA molecules that bind specific ligands, Nature, vol. 346, pp. 818-822, Aug. 30, 1990.
Esmon, The protein C pathway, Crit. Care Med., vol. 28, suppl. 9, pp. S44-S48, Sep. 2000.
Fields; New culprits in chronic pain; Scientific American; pp. 50-57; Nov. 2009.

(56) References Cited

OTHER PUBLICATIONS

Fleshner, M., et al., Thermogenic and corticosterone responses to intravenous cytokines (IL-1? and TNF-?) are attenuated by subdiaphragmatic vagotomy, J. Neuroimmunol., vol. 86(2), pp. 134-141, Jun. 1998.
Fox, D. A., Cytokine blockade as a new strategy to treat rheumatoid arthritis, Arch. Intern. Med., vol. 160, pp. 437-444, Feb. 28, 2000.
Fox, et al., Use of muscarinic agonists in the treatment of Sjorgren' syndrome, Clin. Immunol., vol. 101, No. 3; pp. 249-263, Dec. 2001.
Fujii et al.; Simvastatin regulates non-neuronal cholinergic activity in T lymphocytes via CD11a-mediated pathways; J. Neuroimmunol.; 179(1-2); pp. 101-107; Oct. 2006.
Gao et al.; Investigation of specificity of auricular acupuncture points in regulation of autonomic function in anesthetized rats; Autonomic Neurosc.; 138(1-2); pp. 50-56; Feb. 29, 2008.
Gattorno, M., et al., Tumor necrosis factor induced adhesion molecule serum concentrations in henoch-schoenlein purpura and pediatric systemic lupus erythematosus, J. Rheumatol., vol. 27, No. 9, pp. 2251-2255, Sep. 2000.
Gaykema, R. P., et al., Subdiaphragmatic vagotomy suppresses endotoxin-induced activation of hypothalamic corticotropin-releasing hormone neurons and ACTH secretion, Endocrinology, vol. 136, No. 10, pp. 4717-4720, Oct. 1995.
Ghelardini et al., S-(−)-ET 126: A potent and selective M1 antagonist in vitro and in vivo, Life Sciences, vol. 58, No. 12, pp. 991-1000, Feb. 1996.
Ghia, et al., The vagus nerve: a tonic inhibitory influence associated with inflammatory bowel disease in a murine model, Gastroenterology, vol. 131, No. 4, pp. 1122-1130, Oct. 2006.
Giebelen, at al., Stimulation of ?7 cholinergic receptors inhibits lipopolysaccharide-induced neutrophil recruitment by a tumor necrosis factor ?—independent mechanism, SHOCK, vol. 27, No. 4, pp. 443-447, Apr. 2007.
Goyal et al., Nature of the vagal inhibitory innervation to the lower esophageal sphincter, Journal of Clinical Investigation, vol. 55, pp. 1119-1126, May 1975.
Gracie, J. A., et al., A proinflammatory role for IL-18 in rheumatoid arthritis, J. Clin. Invest., vol. 104, No. 10, pp. 1393-1401, Nov. 1999.
Granert at al., Suppression of macrophage activation with CNI-1493 increases survival in infant rats with systemic haemophilus influenzae infection, Infection and Immunity, vol. 68, No. 9, pp. 5329-5334, Sep. 2000.
Green et al., Feedback technique for deep relaxation, Psycophysiology, vol. 6, No. 3, pp. 371-377, Nov. 1969.
Gregory et al., Neutrophil-kupffer-cell interaction in host defenses to systemic infections, Immunology Today, vol. 19, No. 11, pp. 507-510, Nov. 1998.
Groves et al.; Recordings from the rat locus coeruleus during acute vagal nerve stimulation in the anaesthetised rat; Neuroscience Letters; 379(3); pp. 174-179; May 13, 2005.
Guslandi, M., Nicotine treatment for ulcerative colitis, Br. J. Clin. Pharmacol., vol. 48(4), pp. 481-484, Oct. 1999.
Hansson, E.; Could chronic pain and spread of pain sensation be induced and maintained by glial activation?. Acta Physiologica, vol. 187, Issue 1-2; pp. 321R327, May/Jun. 2006.
Harrison's Principles of Internal Medicine, 13th Ed., pp. 511-515 and 1433-1435, Mar. 1994.
Hatton et al.; Vagal nerve stimulation: overview and implications for anesthesiologists; Intl Anesthesia Research Society; vol. 103; No. 5; pp. 1241-1249; Nov. 2006.
Hirano, T., Cytokine suppresive agent improves survival rate in rats with acute pancreatitis of closed duodenal loop, J. Surg. Res., vol. 81, No. 2, pp. 224-229, Feb. 1999.
Hirao et al., The limits of specificity: an experimental analysis with RNA aptamers to MS2 coat protein variants, Mol. Divers., vol. 4, No. 2, pp. 75-89, 1999 (Accepted Jan. 13, 1999).
Hoffer et al.; Implantable electrical and mechanical interfaces with nerve and muscle; Annals of Biomedical Engineering; vol. 8; pp. 351-360; (year of pub. sufficiently earlier than effective US filed and any foreign priority date) 1980.
Holladay et al., Neuronal nicotinic acetylcholine receptors as targets for drug discovery, Journal of Medicinal Chemistry, 40(26), pp. 4169-4194, Dec. 1997.
Hommes, D. W. et al., Anti- and Pro-inflammatory cytokines in the pathogenesis of tissue damage in Crohn's disease, Current Opinion in Clinical Nutrition and Metabolic Care, vol. 3(3), pp. 191-195, May 2000.
Hsu, et al., Analysis of efficiency of magnetic stimulation, IEEE Trans. Biomed. Eng., vol. 50(11), pp. 1276-1285, Nov. 2003.
Hsu, H. Y., et al., Cytokine release of peripheral blood monocuclear cells in children with chronic hepatitis B virus infection, J. Pediatr. Gastroenterol., vol. 29, No. 5, pp. 540-545, Nov. 1999.
Hu, et al., The effect of norepinephrine on endotoxin-mediated macrophage activation, J. Neuroimmunol., vol. 31(1), pp. 35-42, Jan. 1991.
Huston et al.; Splenectomy inactivates the cholinergic antiinflammatory pathway during lethal endotoxemia and polymicrobial sepsis; J. Exp. Med. 2006; vol. 203, No. 7; pp. 1623-1628; Jun. 19, 2006.
Huston et al.; Transcutaneous vagus nerve stimulation reduces serum high mobility group box 1 levels and improves survival in murine sepsis; Crit. Care Med.; 35(12); pp. 2762-2768; Dec. 2007.
Hutchinson et al.; Proinflammatory cytokines oppose opioid induced acute and chronic analgesia; Brain Behav Immun.; vol. 22; No. 8; pp. 1178-1189; Nov. 2008.
Ilton et al., "Differential expression of neutrophil adhesion molecules during coronary artery surgery with cardiopulmonary bypass" Journal of Thoracic and Cardiovascular Surgery, Mosby-Year Book, inc., St. Louis, Mo, US, pp. 930-937, Nov. 1, 1999.
Jaeger et al., The structure of HIV-1 reverse transcriptase complexed with an Rna pseudoknot inhibitor, The EMBO Journal, 17(15), pp. 4535-4542, Aug. 1998.
Jander, S. et al., Interleukin-18 is induced in acute inflammatory demyelinating polymeuropathy, J. Neuroimmunol., vol. 114, pp. 253-258, Mar. 2001.
Joshi et al., Potent inhibition of human immunodeficiency virus type 1 replection by template analog reverse transcriptase , J. Virol., 76(13), pp. 6545-6557, Jul. 2002.
Kawahara et al.; SIRT6 links histone H3 lysine 9 deacetylation to NF-kappaB-dependent gene expression and organismal life span.; Cell. ; vol. 136; No. 1; pp. 62-74; Jan. 2009.
Kalishevskaya et al. "The character of vagotomy-and atropin-induced hypercoagulation," Sechenov Physiological Journal of the USSR, 65(3): pp. 398-404, Mar. 1979.
Kalishevskaya et al.; Nervous regulation of the fluid state of the blood; Usp. Fiziol. Nauk;,vol. 13; No. 2; pp. 93-122; Apr.-Jun. 1982.
Kanai, T. et al., Interleukin-18 and Crohn's disease, Digestion, vol. 63, suppl. 1, pp. 37-42, (year of pub. sufficiently earlier than effective US filed and any foreign priority date) 2001.
Katagiri, M., et al., Increased cytokine production by gastric mucosa in patients with helicobacter pylon infection, J. Clin, Gastroenterol., vol. 25, Suppl. 1, pp. S211-S214, (year of pub. sufficiently earlier than effective US filed and any foreign priority date) 1997.
Kawashima, et al., Extraneuronal cholinergic system in lymphocytes, Pharmacology & Therapeutics, vol. 86, pp. 29-48, Apr. 2000.
Kees et al; Via beta-adrenoceptors, stimulation of extrasplenic sympathetic nerve fibers inhibits lipopolysaccharide-induced TNF secretion in perfused rat spleen; J.Neuroimmunol.; 145(1-2); pp. 77-85; Dec. 2003.
Kensch et al., HIV-1 reverse transcriptase-pseudoknot RNA aptamer interaction has a binding affinity in the low picomolar range coupled with high specificity, J. Biol. Chem., 275(24), pp. 18271-18278, Jun. 16, 2000.
Khatun, S., et al., "Induction of hypercoagulability condition by chronic localized cold stress in rabbits," Thromb. And Haemost., 81(3): pp. 449-455, Mar. 1999.

(56) References Cited

OTHER PUBLICATIONS

Kimball, et al., Levamisole causes differential cytokine expression by elicited mouse peritoneal macrophases, Journal of Leukocyte Biology, vo. 52, No. 3, pp. 349-356, Sep. 1992 (abstract only).

Kimmings, A. N., et al., Systemic inflammatory response in acute cholangitis and after subsequent treatment, Eur. J. Surg., vol. 166, pp. 700-705, Sep. 2000.

Kirchner et al.; Left vagus nerve stimulation suppresses experimentally induced pain; Neurology; vol. 55; pp. 1167-1171; Oct. 2000.

Kokkula, R. et al., Successful treatment of collagen-induced arthritis in mice and rats by targeting extracellular high mobility group box chromosomal protein 1 activity, Arthritis Rheum., 48(7), pp. 2052-2058, Jul. 2003.

Krarup et al; Conduction studies in peripheral cat nerve using implanted electrodes: I. methods and findings in controls; Muscle & Nerve; vol. 11; pp. 922-932; Sep. 1988.

Kudrjashov, et al. "Reflex nature of the physiological anticoagulating system," Nature, vol. 196(4855): pp. 647-649; Nov. 17, 1962.

Kumins, N. H., et al., Partial hepatectomy reduces the endotoxin-induced peak circulating level of tumor necrosis factor in rats, SHOCK, vol. 5, No. 5, pp. 385-388, May 1996.

Kuznik, "Role of the vascular wall in the process of hemostatis," Usp Sovrem Biol., vol. 75(1): pp. 61-85, (year of pub. sufficiently earlier than effective US filed and any foreign priority date) 1973.

Kuznik, et al., "Blood Coagulation in stimulation of the vagus nerve in cats," Biull. Eskp. Biol. Med., vol. 78 (7): pp. 7-9, (year of pub. sufficiently earlier than effective US filed and any foreign priority date) 1974.

Kuznik, et al., "Heart as an efferent regulator of the process of blood coagulation and fibrinolysis," Kardiologiia, vol. 13(3): pp. 10-17, (year of pub. sufficiently earlier than effective US filed and any foreign priority date) 1973.

Kuznik, et al., "Role of the heart and vessels in regulating blood coagulation and fibrinolysis," Kagdiologiia, vol. 13 (4): pp. 145-154, (year of pub. sufficiently earlier than effective US filed and any foreign priority date) 1973.

Kuznik, et al., "Secretion of blood coagulation factors into saliva under conditions of hypo-and hypercoagulation," Voprosy Meditsinskoi Khimii, vol. 19(1): pp. 54-57; (year of pub. sufficiently earlier than effective US filed and any foreign priority date) 1973.

Kuznik, et al., "The dynamics of procoagulatible and fibrinolytic activities during electrical stimulation of peripheral nerves," Sechenov Physiological Journal of the USSR, vol. 65; No. 3: pp. 414-420, Mar. 1979.

Kuznik, et al., "The role of the vascular wall in the mechanism of control of blood coagulation and fibrinolysis on stimulation of the vagus nerve," Cor Vasa, vol. 17(2): pp. 151-158, (year of pub. sufficiently earlier than effective US filed and any foreign priority date) 1975.

Lang, et al., "Neurogienic control of cerebral blood flow," Experimental Neurology, 43(1): pp. 143-161, Apr. 1974.

Lee, H. G., et al., Peritoneal lavage fluids stimulate NIH3T3 fibroblast proliferation and contain increased tumour necrosis factor and IL6 in experimental silica-induced rat peritonitis, Clin. Exp. Immunol., vol. 100, pp. 139-144, Apr. 1995.

LeNovere, N. et al., Molecular evolution of the nicotinic acetylcholine receptor: an example of multigene family in excitable cells, J. Mol. Evol., 40, pp. 155-172, Feb. 1995.

Leonard, S. et al., Neuronal nicotinic receptors: from structure to function, Nicotine & Tobacco Res. 3:203-223, Aug. 2001.

Lips et al.; Coexpression and spatial association of nicotinic acetylcholine receptor subunits alpha7 and alpha10 in rat sympathetic neurons; J.Mol.Neurosci.; 30; pp. 15-16; (year of pub. sufficiently earlier than effective US filed and any foreign priority date) 2006.

Lipton, J. M. et al.; Anti-inflammatory actions of the neuroimmunomodulator ?—MSH, Immunol. Today, vol. 18, pp. 140-145, Mar. 1997.

Loeb et al.; Cuff electrodes for chronic stimulation and recording of peripheral nerve activity; Journal of Neuroscience Methods; vol. 64; pp. 95-103; Jan. 1996.

Madretsma, G. S., et al., Nicotine inhibits the in vitro production of interleukin 2 and tumour necrosis factor-alpha by human monocuclear cells, Immunopharmacology, vol. 35, No. 1, pp. 47-51, Oct. 1996.

Martindale: The Extra Pharmacopoeia; 28th Ed. London; The pharmaceutical press; pp. 446-485; (year of pub. sufficiently earlier than effective US filed and any foreign priority date) 1982.

Martiney et al., Prevention and treatment of experimental autoimmune encephalomyelitis by CNI-1493, a macrophage-deactivating agent, Journal of Immunology, vol. 160, No. 11, pp. 5588-5595, Jun. 1, 1998.

McGuinness, P. H., et al., Increases in intrahepatic CD68 positive cells, MAC387 positive cells, and proinflammatory cytokines (particulary interleukin 18) in chronic hepatitis C infection, Gut, vol. 46, pp. 260-269, (year of pub. sufficiently earlier than effective US filed and any foreign priority date) 2000.

Miguel-Hidalgo, J.J.; The role of glial cells in drug abuse; Current Drug Abuse Reviews; vol. 2; No. 1; pp. 76-82; Jan. 2009.

Milligan et al.; Pathological and protective roles of glia in chronic pain; Nat Rev Neurosci.; vol. 10; No. 1; pp. 23-26; Jan. 2009.

Minnich et al.; Anti-cytokine and anti-inflammatory therapies for the treatment of severe sepsis: progress and pitfalls; Proceedings of the Nutrition Society; vol. 63(3); pp. 437-441; (year of pub. sufficiently earlier than effective US filed and any foreign priority date) 2004.

Mishchenko, et al., "Coagulation of the blood and fibrinolysos in dogs during vagal stimulation," Sechenov Physiological Journal of the USSR, vol. 61(1): pp. 101-107, (year of pub. sufficiently earlier than effective US filed and any foreign priority date) 1975.

Mishchenko, "The role of specific adreno-and choline-receptors of the vascular wall in the regulation of blood coagulation in the stimulation of the vagus nerve," Biull. Eskp. Biol. Med., vol. 78(8): pp. 19-22, (year of pub. sufficiently earlier than effective US filed and any foreign priority date) 1974.

Molina et al., CNI-1493 attenuates hemodynamic and pro-inflammatory responses to LPS, Shock, vol. 10, No. 5, pp. 329-334, Nov. 1998.

Nadol et al., "Surgery of the Ear and Temporal Bone," Lippinkott Williams & Wilkins, 2nd Ed., 2005, (Publication date: Sep. 21, 2004), p. 580.

Nagashima et al., Thrombin-activatable fibrinolysis inhibitor (TAFI) deficiency is compatible with murine life, J. Clin. Invest., 109, pp. 101-110, Jan. 2002.

Nathan, C. F., Secretory products of macrophages, J. Clin. Invest., vol. 79 (2), pp. 319-326, Feb. 1987.

Navalkar et al.; Irbesartan, an angiotensin type 1 receptor inhibitor, regulates markers of inflammation in patients with premature atherosclerosis; Journal of the American College of Cardiology; vol. 37; No. 2; pp. 440-444; Feb. 2001.

Neuhaus et al.; P300 is enhanced in responders to vagus nerve stimulation for treatment of major depressive disorder; J. Affect. Disord.; 100(1-3); pp. 123-128; Jun. 2007.

Noguchi et al., Increases in Gastric acidity in response to electroacupuncture stimulation of hindlimb of anesthetized rats, Jpn. J. Physiol., 46(1), pp. 53-58, Feb. 1996.

Norton, Can ultrasound be used to stimulate nerve tissue, BioMedical Engineering OnLine, 2(1), pp. 6, Mar. 4, 2003.

Palmblad et al., Dynamics of early synovial cytokine expression in rodent collagen-induced arthritis: a thereapeutic study unding a macrophage-deactivation compound, American Journal of Pathology, vol. 158, No. 2, pp. 491-500, Feb. 2, 2001.

Pateyuk, et al.,"Treatment of Botkin's disease with heparin," Klin. Med., vol. 51(3): pp. 113-117, Mar. 1973.

Pavlov et al; Controlling inflammation: the cholinergic anti-inflammatory pathway; Biochem. Soc. Trans.; 34(Pt 6); pp. 1037-1040; Dec. 2006.

Payne, J. B. et al., Nicotine effects on PGE2 and IL-1 beta release by LPS—treated human monocytes, J. Perio. Res., vol. 31, No. 2, pp. 99-104, Feb. 1996.

(56) References Cited

OTHER PUBLICATIONS

Peuker; The nerve supply of the human auricle; Clin. Anat.; 15(1); pp. 35-37; Jan. 2002.

Prystowsky, J. B. et al., Interleukin-1 mediates guinea pig gallbladder inflammation in vivo, J. Surg. Res., vol. 71, No. 2, pp. 123-126, Aug. 1997.

Pulkki, K. J., Cytokines and cardiomyocyte death, Ann. Med., vol. 29(4), pp. 339-343, Aug. 1997.

Pullan, R. D., et al., Transdermal nicotine for active ulceratiive colitis, N. Engl. J. Med., vol. 330, No. 12, pp. 811-815, Mar. 24, 1994.

Pulvirenti et al; Drug dependence as a disorder of neural plasticity:focus on dopamine and glutamate; Rev Neurosci.; vol. 12; No. 2; pp. 141-158; Apr./Jun. 2001.

Rayner, S. A. et al., Local bioactive tumour necrosis factor (TNF) in corneal allotransplantation, Clin. Exp. Immunol., vol. 122, pp. 109-116, Oct. 2000.

Reale et al.; Treatment with an acetylcholinesterase inhibitor in alzheimer patients modulates the expression and production of the pro-inflammatory and anti-inflammatory cytokines; J. Neuroimmunology; 148(1-2); pp. 162-171; Mar. 2004.

Rinner et al.; Rat lymphocytes produce and secrete acetylcholine in dependence of differentiation and activation; J.Neuroimmunol.; 81(1-2); pp. 31-37; Jan. 1998.

Robinson et al.; Studies with the Electrocardiograph on the Action of the Vagus Nerve on the Human Heart; J Exp Med; 14(3):217-234; Sep. 1911.

Romanovsky, A. A., et al.,The vagus nerve in the thermoregulatory response to systemic inflammation, Am. J. Physiol., vol. 273, No. 1 (part 2), pp. R407-R413, Jul. 1, 1997.

Saghizadeh et al.; The expression of TNF? by human muscle; J. Clin. Invest.; vol. 97; No. 4; pp. 1111-1116; Feb. 15, 1996.

Saindon et al.; Effect of cervical vagotomy on sympathetic nerve responses to peripheral interleukin-1beta; Auton.Neuroscience Basic and Clinical; 87; pp. 243-248; Mar. 23, 2001.

Saito, Involvement of muscarinic M1 receptor in the central pathway of the serotonin-induced bezold-jarisch reflex in rats, J. Autonomic Nervous System, vol. 49, pp. 61-68, Sep. 1994.

Sandborn, W. J., et al., Transdermal nicotine for mildly to moderately active ulcerative colitis, Ann. Intern. Med, vol. 126, No. 5, pp. 364-371, Mar. 1, 1997.

Sato, E., et al., Acetylcholine stimulates alveolar macrophages to release inflammatory cell chemotactic activity, Am. J. Physiol., vol. 274, pp. L970-L979, Jun. 1998.

Sato, K.Z., et al., Diversity of mRNA expression for muscarinic acetylcholine receptor subtypes and neuronal nicotinic acetylcholine receptor subunits in human mononuclear leukocytes and leukemic cell lines, Neuroscience Letters, vol. 266, pp. 17-20, Apr. 30, 1999.

Scheinman, R. I., et al., Role of transcriptional activation of I?B? in mediation of immunosuppression by glucocorticoids, Science, vol. 270, No. 5234, pp. 283-286, Oct. 13, 1995.

Schneider et al., High-affinity ssDNA inhibitors of the review transcriptase of type 1 human immunodeficiency virus, Biochemistry, 34(29), pp. 9599-9610, (year of pub. sufficiently earlier than effective US filed and any foreign priority date) 1995.

Shafer, Genotypic testing for human immunodeficiency virus type 1 drug resistance, Clinical Microbiology Reviews, vol. 15, pp. 247-277, Apr. 2002.

Shapiro et al.; Prospective, randomised trial of two doses of rFVIIa (NovoSeven) in haemophilia patients with inhibitors undergoing surgery; Thromb Haemost; vol. 80(5); pp. 773-778; Nov. 1998.

Sher, M. E., et al., The influence of cigarette smoking on cytokine levels in patients with inflammatory bowel disease, Inflamm. Bowel Dis., vol. 5, No. 2, pp. 73-78, May 1999.

Shi et al.; Effects of efferent vagus nerve excitation on inflammatory response in heart tissue in rats with endotoxemia; vol. 15, No. 1; pp. 26-28; Jan. 2003 (Eng. Abstract).

Snyder et al., Correction of hemophilia B in canine and murine models using recombinant adeno-associated viral vectors; Nature Medicine, 5(1), pp. 64-70, Jan. 1999.

Sokratov, et al. "The role of choline and adrenegic structures in regulation of renal excretion of hemocoagulating compounds into the urine," Sechenov Physiological Journal of the USSR, vol. 63(12): pp. 1728-1732, (year of pub. sufficiently earlier than effective US filed and any foreign priority date) 1977.

Stalcup et al., Endothelial cell functions in the hemodynamic responses to stress, Annals of the New York Academy of Sciences, vol. 401, pp. 117-131, Dec. 1982.

Steinlein, New functions for nicotine acetylcholine receptors?, Behavioural Brain Res., vol. 95, pp. 31-35, (year of pub. sufficiently earlier than effective US filed and any foreign priority date) 1998.

Sternberg, E. M., Perspectives series: cytokines and the brain 'neural-immune interactions in health and disease,' J. Clin. Invest., vol. 100, No. 22, pp. 2641-2647, Dec. 1997.

Stevens et al.; The anti-inflammatory effect of some immunosuppressive agents; J. Path.; 97(2); pp. 367-373 (year of pub. sufficiently earlier than effective US filed and any foreign priority date); 1969.

Strojnik et al.; Treatment of drop foot using and implantable peroneal underknee stimulator; Scand. J. Rehab. Med.; vol. 19(1); pp. 37R43; (year of pub. sufficiently earlier than effective US filed and any foreign priority date) 1987.

Sugano et al., Nicotine inhibits the production of inflammatory mediators in U937 cells through modulation of nuclear factor-kappaβ activation, Biochemical and Biophysical Research Communications, vol. 252, No. 1, pp. 25-28, Nov. 9, 1998.

Suter et al.; Do glial cells control pain?; Neuron Glia Biol.; vol. 3; No. 3; pp. 255-268; Aug. 2007.

Swick et al.; Locus coeruleus neuronal activity in awake monkeys: relationship to auditory P300-like potentials and spontaneous EEG. Exp. Brain Res.; 101(1); pp. 86-92; 1994 (year of pub. sufficiently earlier than effective US filed and any foreign priority date).

Sykes, et al., An investigation into the effect and mechanisms of action of nicotine in inflammatory bowel disease, Inflamm. Res., vol. 49, pp. 311-319, Jul. 2000.

Takeuchi et al., A comparision between chinese blended medicine "Shoseiryuto" tranilast and ketotifen on the anit-allergic action in the guinea pigs, Allergy, vol. 34, No. 6, pp. 387-393, Jun. 1985 (eng. abstract).

Tekdemir et al.; A clinico-anatomic study of the auricular branch of the vagus nerve and arnold's ear-cough reflex; Surg. Radiol. Anat.; 20(4); pp. 253-257; Mar. 1998.

Toyabe, et al., Identification of nicotinic acetylcholine receptors on lymphocytes in the periphery as well as thymus in mice, Immunology, vol. 92(2), pp. 201-205, Oct. 1997.

Tracey et al., Mind over immunity, Faseb Journal, vol. 15, No. 9, pp. 1575-1576, Jul. 2001.

Tracey, K. J. et al., Anti-cachectin/TNF monoclonal antibodies prevent septic shock during lethal bacteraemia; Nature, 330: pp. 662-664, Dec. 23, 1987.

Tracey, K. J. et al., Physiology and immunology of the cholinergic antiinflammatory pathway; J Clin Invest.; vol. 117: No. 2; pp. 289-296; Feb. 2007.

Tracey, K. J.; Reflex control of immunity; Nat Rev Immunol; 9(6); pp. 418-428; Jun. 2009.

Tracey, K. J. et al., Shock and tissue injury induced by recombinant human cachectin, Science, vol. 234, pp. 470-474, Oct. 24, 1986.

Tracey, K.J., The inflammatory reflex, Nature, vol. 420, pp. 853-859, Dec. 19-26, 2002.

Tsutsui, H., et al., Pathophysiolocical roles of interleukin-18 in inflammatory liver diseases; Immunol. Rev., 174:192-209, Apr. 2000.

Tuerk et al., RNA pseudoknots that inhibit human immunodeficiency virus type 1 reverse transcriptase; Proc. Natl. Acad. Sci. USA, 89, pp. 6988-6992, Aug. 1992.

Tuerk et al., Systematic evolution of ligands by exponential enrichment: RNA ligands to bacteriophage T4 DNA polymerase; Science, 249(4968), pp. 505-510, Aug. 3, 1990.

(56) References Cited

OTHER PUBLICATIONS

Van Dijk, A. P., et al., Transdermal nictotine inhibits interleukin 2 synthesis by mononuclear cells derived from healthy volunteers, Eur. J. Clin. Invest, vol. 28, pp. 664-671, Aug. 1998.

Van Der Horst et al.; Stressing the role of FoxO proteins in lifespan and disease; Nat Rev Mol Cell Biol.; vol. 8; No. 6; pp. 440-50; Jun. 2007.

Vanhoutte, et al., Muscarinic and beta-adrenergic prejunctional modulation of adrenergic neurotransmission in the blood vessel wall, Gen Pharmac., vol. 14, pp. 35-37, (year of pub. sufficiently earlier than effective US filed and any foreign priority date) 1983.

vanWesterloo, et al., The cholinergic anti-inflammatory pathway regulates the host response during septic peritonitis, The Journal of Infectious Diseases, vol. 191, pp. 2138-2148, Jun. 15, 2005.

Ventureyra, Transcutaneous vagus nerve stimulation for partial onset seizure therapy, Child's Nery Syst, vol. 16(2), pp. 101-102, (year of pub. sufficiently earlier than effective US filed and any foreign priority date) 2000.

Vijayaraghavan, S.; Glial-neuronal interactions-implications for plasticity anddrug addictionl AAPS J.; vol. 11; No. 1; pp. 123-132; Mar. 2009.

Villa et al., Protection against lethal polymicrobial sepsis by CNI-1493, an inhibitor of pro-inflammatory cytokine synthesis, Journal of Endotoxin Research, vol. 4, No. 3, pp. 197-204, Jun. 1997.

Von Känel, et al., Effects of non-specific ?-adrenergic stimulation and blockade on blood coagulation in hypertension, J. Appl. Physiol., vol. 94, pp. 1455-1459, Apr. 2003.

Von Känel, et al., Effects of sympathetic activation by adrenergic infusions on hemostasis in vivo, Eur. J. Haematol., vol. 65: pp. 357-369, Dec. 2000.

Walland et al., Compensation of muscarinic brochial effects of talsaclidine by concomitant sympathetic activation in guinea pigs; European Journal of Pharmacology, vol. 330(2-3), pp. 213-219, Jul. 9, 1997.

Wang et al; Nicotinic acetylcholine receptor alpha7 subunit is an essential regulator of inflammation; Nature; 421; 384-388; Jan. 23, 2003.

Wang, H., et al., HMG-1 as a late mediator of endotoxin lethality in mice, Science, vol. 285, pp. 248-251, Jul. 9, 1999.

Waserman, S. et al., TNF-? dysregulation in asthma: relationship to ongoing corticosteroid therapy, Can. Respir. J., vol. 7, No. 3, pp. 229-237, May-Jun. 2000.

Watanabe, H. et al., The significance of tumor necrosis factor (TNF) levels for rejection of joint allograft, J. Reconstr. Microsurg., vol. 13, No. 3, pp. 193-197, Apr. 1997.

Wathey, J.C. et al., Numerical reconstruction of the quantal event at nicotinic synapses; Biophys. J., vol. 27: pp. 145-164, Jul. 1979.

Watkins, L.R. et al., Blockade of interleukin-1 induced hyperthermia by subdiaphragmatic vagotomy: evidence for vagal mediation of immune-brain communication, Neurosci. Lett., vol. 183(1-2), pp. 27-31, Jan. 1995.

Watkins, L.R. et al., Implications of immune-to-brain communication for sickness and pain, Proc. Natl. Acad. Sci. U.S.A., vol. 96(14), pp. 7710-7713, Jul. 6, 1999.

Webster's Dictionary, definition of "intrathecal", online version accessed Apr. 21, 2009.

Weiner, et al., "Inflammation and therapeutic vaccination in CNS diseases," Nature., vol. 420(6917): pp. 879-884, Dec. 19-26, 2002.

Westerheide et al.; Stress-inducible regulation of heat shock factor 1 by the deacetylase SIRT1.; Science; Vo. 323; No. 5717; pp. 1063-1066; Feb. 2009.

Whaley, K. et al., C2 synthesis by human monocytes is modulated by a nicotinic cholinergic receptor, Nature, vol. 293, pp. 580-582, Oct. 15, 1981.

Woiciechowsky, C. et al., Sympathetic activation triggers systemic interleukin-10 release in immunodepression induced by brain injury, Nature Med., vol. 4, No. 7, pp. 808-813, Jul. 1998.

Yen, S.S. et al., Geriatric cachexia: the role of cytokines, Am. J. Clin. Nutr., vol. 70(2), pp. 183-197, Aug. 1999.

Zamotrinsky et al.; Vagal neurostimulation in patients with coronary artery disease; Auton. Neurosci.; 88(1-2); pp. 109-116; Apr. 2001.

Zhang et al., Tumor necrosis factor, The Cytokine Handbook, 3rd ed., Ed. Thompson, Academic Press, pp. 517-548, Jul. 1, 1998.

Zhang et al.; Chronic vagus nerve stimulation improves autonomic control and attenuates systemic inflammation and heart failure progression in a canine high-rate pacing model; Circulation Heart Fail.; 2; pp. 692-699; Nov. 2009.

Levine et al.; U.S. Appl. No. 14/782,715 entitled "Closed-loop vagus nerve stimulation," filed Oct. 6, 2015.

Faltys et al.; U.S. Appl. No. 14/887,192 entitled "Neural stimulation devices and systems for treatment of chronic inflammation," filed Oct. 19, 2015.

Levine et al.; U.S. Appl. No. 14/922,022 entitled "Systems and methods for stimulating and/or monitoring loci in the brain to treat inflammation and to enhance vagus nerve stimulation," filed Oct. 23, 2015.

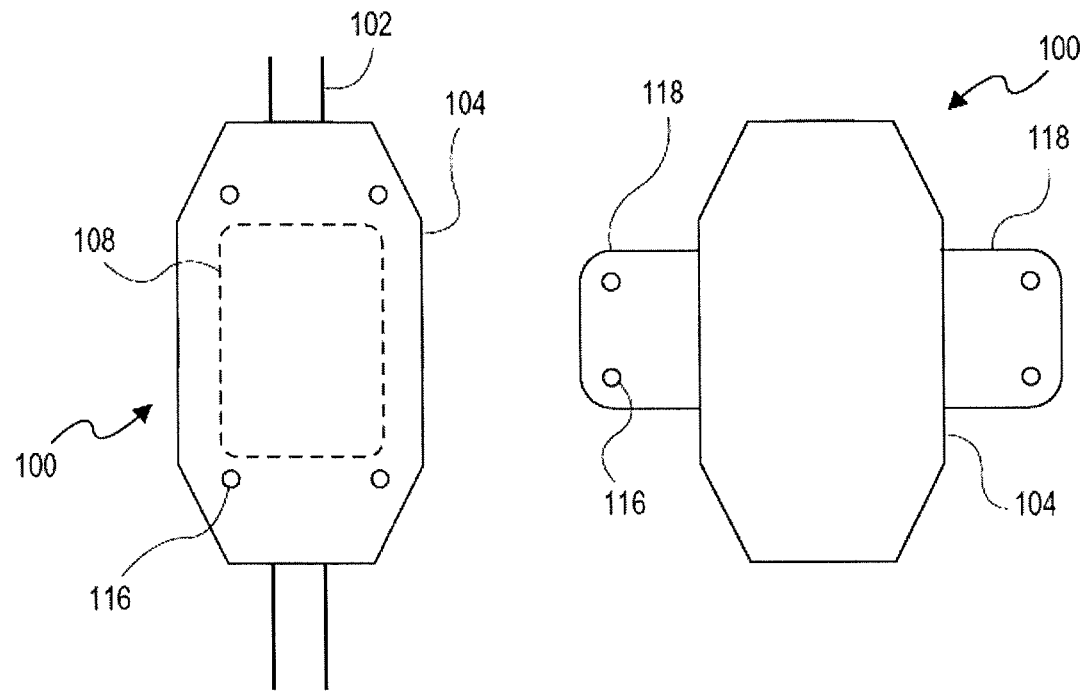
FIG. 3  FIG. 4
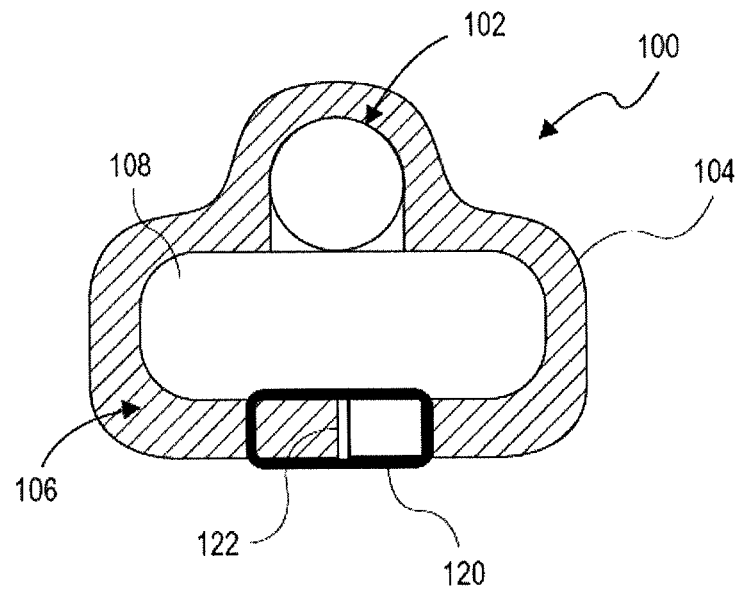
FIG. 5

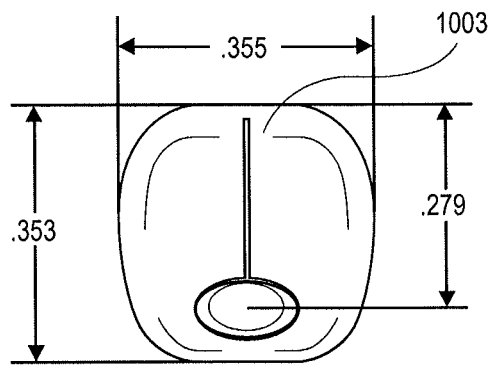
FIG. 10A
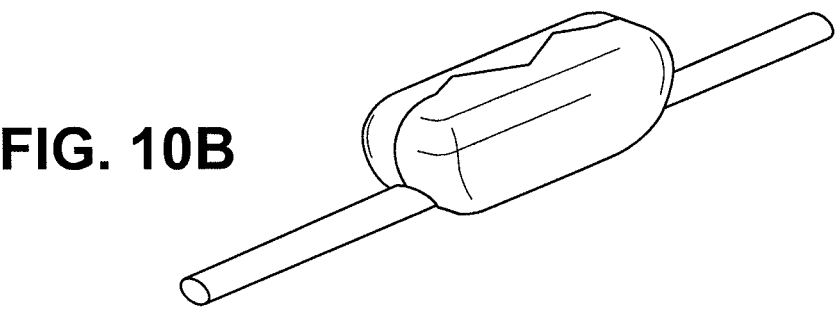
FIG. 10B
FIG. 10C
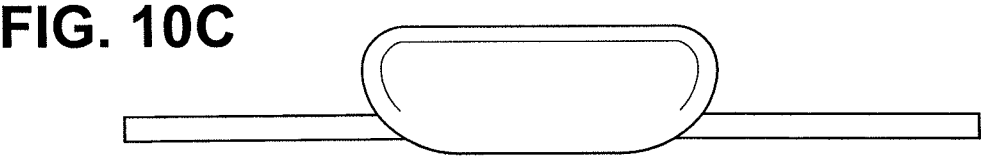
FIG. 10D
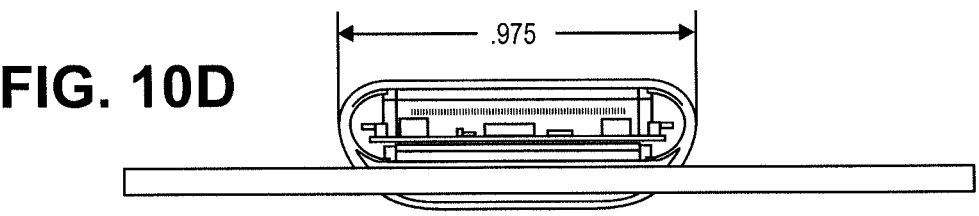

1. Cervical Incision on Lange's Crease

2. Cut Down

3. Expose Nerve

4. Place Pod under nerve

5. Place stimulator in POD

6. Suture POD Closed

7. Use Surgical Tester to verify operation

8. Close Cervical Incision

NERVE CUFF WITH POCKET FOR LEADLESS STIMULATOR

CROSS REFERENCE TO RELATED APPLICATION

This application is a continuation of U.S. patent application Ser. No. 14/536,461, filed Nov. 7, 2014, titled "NERVE CUFF WITH POCKET FOR LEADLESS STIMULATOR," now U.S. Pat. No. 9,174,041, which is a divisional of U.S. patent application Ser. No. 12/797,452, filed Jun. 9, 2010, titled "NERVE CUFF WITH POCKET FOR LEADLESS STIMULATOR, now U.S. Pat. No. 8,886,339, which claims the benefit under 35 U.S.C. §119 of U.S. Provisional Patent Application No. 61/185,494, filed on Jun. 9, 2009, titled "NERVE CUFF WITH POCKET FOR LEADLESS STIMULATOR," each of which is herein incorporated by reference in its entirety.

INCORPORATION BY REFERENCE

All publications and patent applications mentioned in this specification are herein incorporated by reference to the same extent as if each individual publication or patent application was specifically and individually indicated to be incorporated by reference.

FIELD OF THE INVENTION

The present invention relates generally to implantable neural stimulators, and more specifically to a nerve cuff with a pocket for removably receiving an active leadless stimulation device, and methods of stimulating a nerve using such nerve cuff.

BACKGROUND OF THE INVENTION

Implantable electrical stimulation devices have been developed for therapeutic treatment of a wide variety of diseases and disorders. For example, implantable cardioverter defibrillators (ICDs) have been used in the treatment of various cardiac conditions. Spinal cord stimulators (SCS), or dorsal column stimulators (DCS), have been used in the treatment of chronic pain disorders including failed back syndrome, complex regional pain syndrome, and peripheral neuropathy. Peripheral nerve stimulation (PNS) systems have been used in the treatment of chronic pain syndromes and other diseases and disorders. Functional electrical stimulation (FES) systems have been used to restore some functionality to otherwise paralyzed extremities in spinal cord injury patients.

Typical implantable electrical stimulation systems can include a system with one or more programmable electrodes on a lead that are connected to an implantable pulse generator (IPG) that contains a power source and stimulation circuitry. However, these systems can be difficult and/or time consuming to implant, as the electrodes and the IPG are usually implanted in separate areas and therefore the lead must be tunneled through body tissue to connect the IPG to the electrodes. Also, leads are susceptible to mechanical damage over time as they are typically thin and long.

Recently, small implantable neural stimulator technology, i.e. microstimulators, having integral electrodes attached to the body of a stimulator has been developed to address the disadvantages described above. This technology allows the typical IPG, lead and electrodes described above to be replaced with a single device. Elimination of the lead has several advantages including reduction of surgery time by eliminating, for example, the need for implanting the electrodes and IPG in separate places, the need for a device pocket, tunneling to the electrode site, and strain relief ties on the lead itself. Reliability is therefore increased significantly, especially in soft tissue and across joints because active components, such as lead wires, are now part of the rigid structure and are not subject to the mechanical damage due to repeated bending or flexing over time.

However, the leadless integral devices tend to be larger and more massive than the electrode/lead assemblies, making it difficult to stably position the device in the proper position in respect to a nerve. Without device stability, the nerve and/or surrounding muscle or tissue can be damaged due to movement of the assembly.

There remains a need for a leadless integral device that is stably positioned on the nerve, and can provide for removal and/or replacement of the stimulation device with relative ease.

SUMMARY OF THE INVENTION

Described herein are extravascular nerve cuffs for securing a leadless, integral, implantable device to a nerve. The nerve cuff typically includes a pouch or pocket. The cuff electrode configuration of the stimulation device allows the device to be stably positioned proximate a nerve, such as the vagus nerve. Furthermore, the cuff electrode configuration also has the characteristics of driving most of the current into the nerve, while shielding surrounding tissues from unwanted stimulation. Methods of securing a leadless microstimulator using such nerve cuffs are also described herein, as well as methods of stimulating a nerve using microstimulators secured using such cuffs.

There are numerous advantages to using leadless cuffs with a microstimulator, including a decrease in encapsulation (e.g., to about 100 microns) compared to systems without leadless cuffs, since there is less "tugging" on the leadless cuff. Furthermore, leadless cuffs, which may securely attach to a nerve and hold a microstimulator in position, may allow a microstimulator to be modified or replaced while maintaining the same positioning relative to the nerve.

In one embodiment of the invention, the nerve cuff generally includes a cuff body or carrier, made of a flexible material such as a medical-grade soft polymeric material (e.g., Silastic™ or Tecothane™) forming a cuff or sleeve, having a pocket or pouch defined therein for removably receiving a leadless stimulation device. The leadless stimulation device is positioned within the pocket or sleeve such that the electrodes of the device are positioned proximate the nerve to be stimulated. The pocket can be defined by the space between the stimulation device and an inner surface of the cuff body or can comprise a pouch-like structure attached to the cuff body for containing the stimulation device. The nerve cuff can be coupled to the nerve, a surrounding sheath that contains the nerve, or both depending on the desired level of stability.

The nerve cuff can be implanted by first dissecting the nerve, such as the vagus nerve, from its surrounding sheath, wrapping the nerve cuff around the nerve, coupling or suturing the nerve cuff to one of either the nerve or the sheath and inserting the stimulation device within the pocket or pouch of the cuff body such that the stimulation device is proximate the nerve.

For example, described herein are nerve cuffs for securing a leadless microstimulator in stable communication with a nerve. A nerve cuff may include: a cuff body having a channel extending within the length of the cuff body for passage of a nerve; a pocket within the cuff body, configured to removably hold the leadless microstimulator; and an elongate opening slit extending the length of the cuff body configured to be opened to provide access to the pocket.

The nerve cuff may also include an internal electrical contact within the cuff body. For example, the internal electrical contact may be configured to electrically couple the microstimulator and the nerve. In some variations, the nerve further includes an external electrical contact on the outer surface of the cuff body configured to couple with the microstimulator.

In some variations, the cuff body comprises shielding configured to electrically isolate the microstimulator within the nerve cuff. The cuff body may be of uniform thickness, or it may have a non-uniform thickness. For example, the cuff body may have a thickness between about 5 and about 20 mils.

In some variations, the outer surface of the nerve cuff is substantially smooth and atraumatic. The nerve outer surface of the nerve cuff may be rounded and/or conforming. For example, the body may conform to the region of the body into which the cuff and/or microstimulator are implanted.

In some variations, the channel comprises a support channel configured to support the nerve within therein, to prevent pinching of the nerve.

The elongate opening slit may extend the length of the cuff body in an interlocking pattern. In some variations, the slit extends along the side of the cuff body, adjacent to the channel. In other variations, the slit extends along the top of the cuff body, opposite to the channel.

The nerve cuff may also include one or more attachment sites in the elongate opening slit configured to help secure the slit closed. For example, the attachment sites may be holes or passages for a suture.

In some variations, the cuff body is formed of a flexible and biocompatible polymer (e.g., a polymeric biocompatible material such as a silicone polymer.

Also described herein are nerve cuffs for securing a leadless microstimulator in stable communication with a nerve, comprising: an insulating cuff body having a nerve channel extending within the length of the cuff body for passage of a nerve, wherein the cuff body electrically isolates the microstimulator within the cuff body; a conductive surface within the nerve channel configured to engage one or more electrical contacts on the microstimulator; a pocket within the cuff body, configured to removably hold the leadless microstimulator; and an elongate opening slit extending the length of the cuff body configured to be opened to provide access to the pocket.

As mentioned above, the nerve cuff may include one or more external electrical contact on the outer surface of the cuff body configured to couple with the micro stimulator.

In some variations, the nerve cuff body has a uniform thickness; in other variations, the nerve cuff body has a non-uniform thickness. The cuff body may have a thickness between about 5 and about 20 mils.

The outer surface of the nerve cuff may be substantially smooth and atraumatic. For example, the outer surface of the nerve cuff may be contoured.

In some variations, channel through the nerve cuff comprises a support channel configured to support the nerve within therein, to prevent pinching of the nerve.

In some variations, the elongate opening slit extends the length of the cuff body in an interlocking pattern. For example, the interlocking pattern may be a zig-zag pattern, or a sinusoidal pattern.

Also described herein are methods of implanting a leadless microstimulator in communication with a vagus nerve, the method comprising: exposing a vagus nerve; opening a slit of a nerve cuff having a nerve cuff body, wherein the slit opens along the length of the nerve cuff body; placing the nerve cuff around the vagus nerve so that the nerve is within a channel extending the length of nerve cuff; inserting a leadless microstimulator within a pocket in the nerve cuff; and securing the slit of the nerve cuff closed so that the leadless microstimulator is in electrical communication with the nerve and electrically isolated within the nerve cuff body.

In some variations, the step of securing the opening slit of the nerve cuff closed comprises securing the slit so that the leadless microstimulator engages an internal electrical contact within the nerve cuff body. The leadless microstimulator may engage an internal electrical contact configured to provide circumferential stimulation around the nerve within the channel.

The step of securing may comprise suturing the slit closed. In some variations, the slit may be self-closing. For example, there may be enough tension in the cuff to keep it closed by itself. In some variations, dissolvable sutures may be used to keep it closed until the body encapsulates it.

The method may also include the step of testing the microstimulator to confirm electrical communication with the nerve.

In some variations, the step of placing the nerve cuff comprises placing an oversized nerve cuff around the vagus nerve.

Also described herein are methods of implanting a leadless microstimulator in communication with a vagus nerve including the steps of: exposing a vagus nerve; opening a slit of a nerve cuff having a nerve cuff body, wherein the slit opens along the length of the nerve cuff body; placing the nerve cuff around the vagus nerve so that the nerve is within a channel extending the length of nerve cuff; inserting a leadless microstimulator within a pocket in the nerve cuff so that the microstimulator communicates with one or more internal electrical contacts within the nerve cuff; and closing the slit of the nerve cuff so that the nerve is in electrical communication with the one or more internal electrical contact.

In some variations, the leadless microstimulator and the internal electrical contact is configured to provide circumferential stimulation around the nerve within the channel. The step of closing may include the step of securing the slit of the nerve cuff closed. For example, the step of closing may comprise suturing the slit closed. The step of placing the nerve cuff may comprise placing an oversized nerve cuff around the vagus nerve.

The above summary of the invention is not intended to describe each illustrated embodiment or every implementation of the present invention. The figures and the detailed description that follow more particularly exemplify these embodiments.

BRIEF DESCRIPTION OF THE DRAWINGS

FIG. 3 is a front view depicting an implanted nerve cuff with suture holes according to an embodiment of the invention;

FIG. 4 is an open view depicting the nerve cuff with suture holes of FIG. 3;

FIG. 5 is a top view depicting a closing device for the implanted nerve cuff of FIG. 1;

FIG. 7B is a front view of the nerve cuff of FIG. 7a.

FIG. 8B is a front view of the nerve cuff of FIG. 8a; and

FIGS. 10A-10D illustrate one variation of a nerve cuff as described herein. FIG. 10A shows an end view, FIG. 10B is a side perspective view, FIG. 10C is a side view, and FIG. 10D is a longitudinal section through the device attached to a nerve, showing internal features including a microstimulator.

FIG. 11A shows an end view, FIG. 11B is a side perspective view, FIG. 11C is a side view, and FIG. 11D is a longitudinal section through the device attached to a nerve, showing internal features including a microstimulator.

Figure 1:
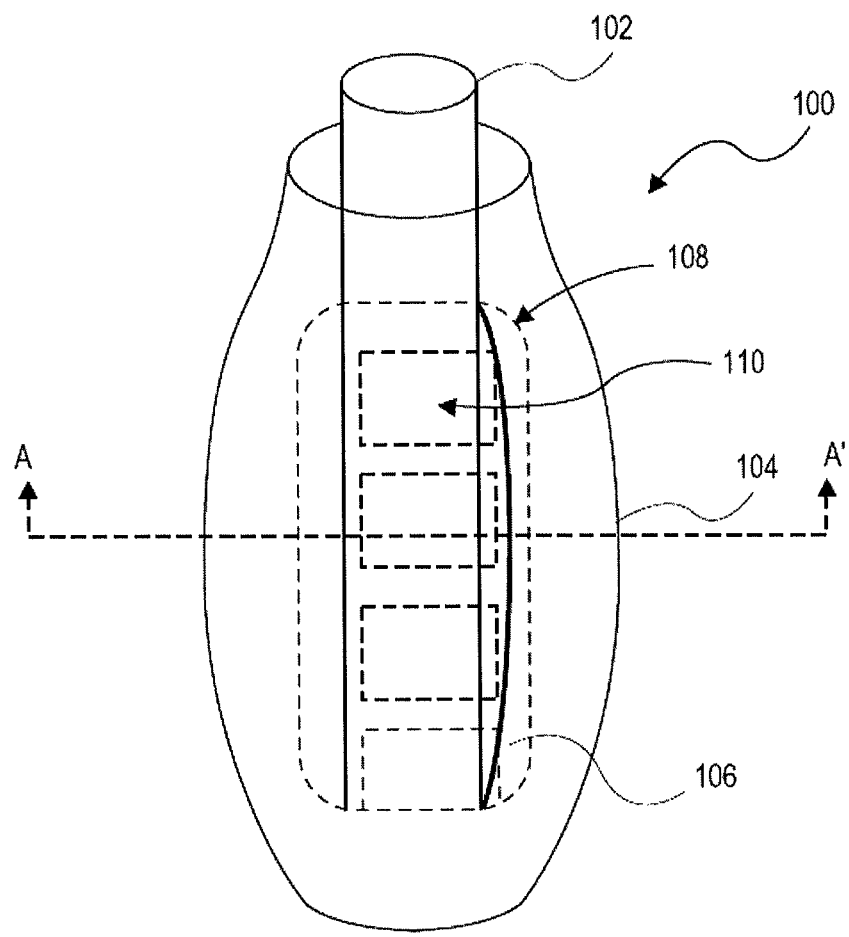
FIG. 1 is a perspective view depicting a nerve cuff with stimulation device implanted proximate a nerve, according to an embodiment of the invention.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

DETAILED DESCRIPTION OF THE INVENTION

Embodiments of the invention are directed to a retaining device, such as a carrier or cuff, which positions active contacts, i.e. electrodes, of a stimulation device against the targeted nerve directing the current from the electrodes into the nerve. The retaining device also inhibits or prevents the current from flowing out to the surrounding tissue.

Referring to FIG. 1, one example of a nerve cuff 100 adapted for holding a stimulation device is coupled to a nerve 102. Nerve 102 can comprise any nerve in the human body targeted for therapeutic treatment, such as, for example, the vagus nerve. Nerve cuff adapter 100 generally comprises an outer carrier or cuff 104 body that can comprise any of a variety of medical grade materials, such as, for example, Silastic™ brand silicone elastomers, or Tecothane™ polymer.

Figure 1A:
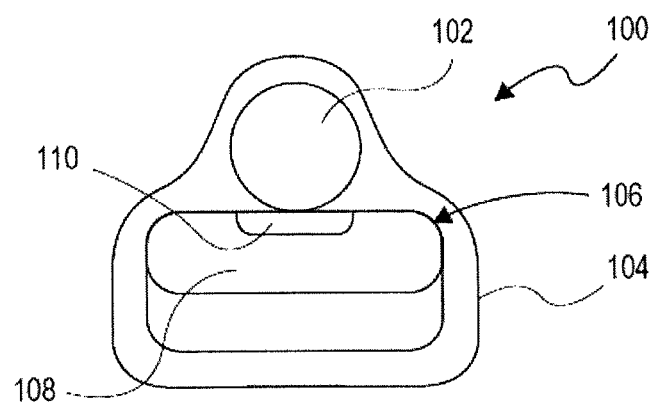
FIG. 1A is a top view depicting the implanted nerve cuff with stimulation device of FIG. 1.

In general, a nerve cuff including a cuff 104 body having (or forming) a pouch or pocket 106 for removably receiving an active, implantable stimulation device 108 having one or more integrated, leadless electrodes 110 on a surface of stimulation device 108 proximate nerve 102. As illustrated in FIGS. 1 and 1A, nerve cuff 100 wraps around nerve 102 such that electrodes 110 are positioned proximate nerve 102.

Figure 1B:
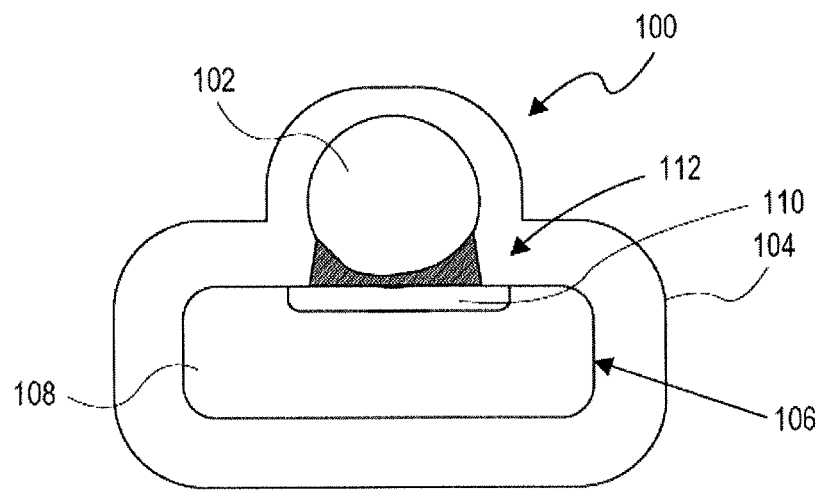
FIG. 1B is a top view depicting the implanted nerve cuff with stimulation device according to an alternative embodiment of the invention.

Contacts or electrodes 110 can be positioned directly against nerve 102, as illustrated in FIG. 1A, or in close proximity to nerve 102, as illustrated in FIG. 1B. Referring specifically to FIG. 1B, close proximity of electrodes 110 and nerve 102 will leave a gap or space 112 that may naturally be filled with fluid or connective tissue. In one embodiment of the invention, electrodes 110 and/or the inner surface of cuff body 104 can include optional steroid coatings to aid in reducing the local inflammatory response and high impedance tissue formation.

In one embodiment, the pocket 106 for containing the stimulation device 108 is defined by the open space between the nerve 102 and the inner surface of the cuff body 104. Stimulation device 108 can be passively retained within pocket 106 by the cuff body 104, or can be actively retained on cuff body with fastening means, such as, for example, sutures. In other embodiments, pocket 106 can comprise a pouch-like structure attached to cuff body 104 into which stimulation device 108 can be inserted. Stimulation device 108 can be passively retained within a pouch-like pocket by simply inserting the device 108 into the pocket or can be actively retained with fastening means. A pouch-like pocket can be positioned either in the interior or on the exterior of cuff body 104. Pouch-like pocket 106 and/or cuff body 104 can include access openings to allow electrodes to be positioned directly proximate or adjacent to nerve 102.

Figure 9A:
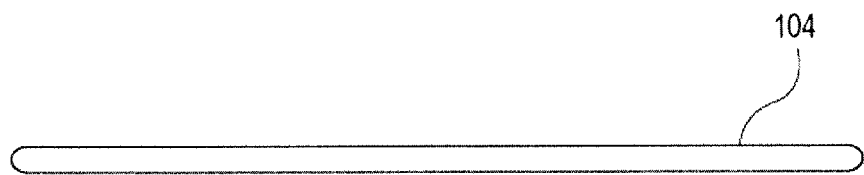
FIGS. 9A and 9B show side views through a section of the cuff body wall, indicating uniform and varying thicknesses, respectively.
Figure 9B:
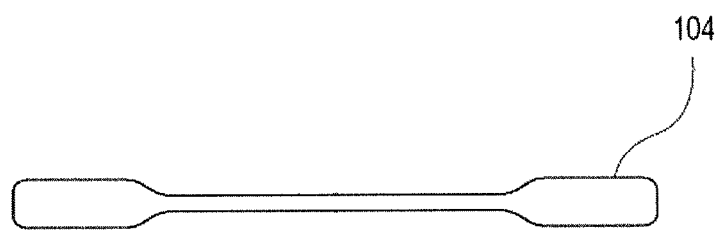

Cuff body 104 can have a constant thickness or a varying thickness as depicted in FIGS. 9A and 9B. The thickness of cuff body 104 can be determined to reduce the palpable profile of the device once the stimulation device is inserted. In one embodiment, the thickness of cuff body can range from about 1 to about 30 mils, or from about 5 to about 20 mils. In one embodiment shown in FIG. 9B, cuff 104 can have a greater thickness at a top and bottom portion of the cuff and a smaller thickness in a middle portion where the stimulation device is contained.

Figure 2:
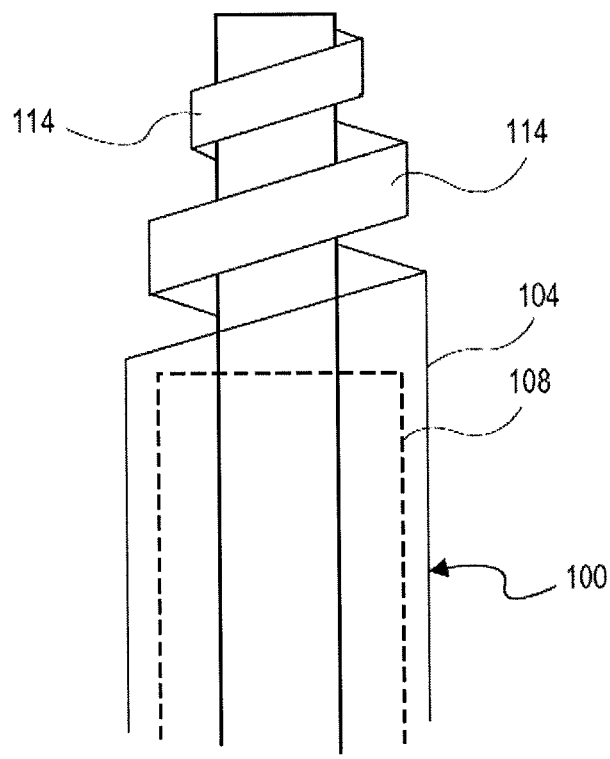
FIG. 2 is a front view depicting an implanted nerve cuff with strain relief according to an embodiment of the invention.

A key obstacle to overcome with implanting stimulation devices proximate nerves or nerve bundles is attaching a rigid structure that makes up the stimulation device along a fragile nerve in soft tissue. In one embodiment of the invention, this issue is resolved by encasing nerve 102 and device 108 in a cuff body 104 that comprises a low durometer material (e.g., Silastic™ or Tecothane™) as described above, that conforms around nerve 102. Further, as illustrated in FIG. 2, cuff body 104 can comprise strain reliefs 114 on its ends that reduce or prevent extreme torsional rotation and keep nerve 102 from kinking. Strain reliefs 114 can coil around nerve 102, and are trimmable to a desired size, such as the size of nerve 102. Further, strain relief 114 can be tapered. In some variations, the lateral ends of the nerve cuff, forming the channel into which the nerve may be place, are tapered and have a tapering thickness, providing some amount of support for the nerve. In some variations, the channel through the nerve cuff in which the nerve may sit, is reinforced to prevent or limit axial loading (e.g., crushing) of the nerve or associated vascular structures when the nerve is within the cuff.

Given the design or architecture of cuff body 104, any vertical movement of cuff body 104 on nerve 102 is not critical to electrical performance, but can result in friction between device 108 and nerve 102 that could potentially damage nerve 102. For that reason, device 108 should readily move up and down nerve 102 without significant friction while being sufficiently fixated to nerve 102 so that eventually connective tissue can form and aid in holding device 108 in place. The challenge is stabilizing device 108 so that it can be further biologically stabilized by connective tissue within several weeks.

Nerve cuff 100 should not be stabilized to surrounding muscle or fascia that will shift relative to the nerve. Therefore, referring to FIGS. 3 and 4, nerve cuff 100 can further comprise connection devices, such as suture holes or suture tabs, for coupling and stabilizing cuff body 104 with device 108 to at least one of the nerve bundle or nerve 102, and the surrounding sheath that contains nerve 102. In one embodiment of the invention, for example, as shown in FIG. 3, cuff body 104 can comprise suture holes 116 that can be used with sutures to couple cuff 104 body with device 108 to the surrounding nerve sheath. In an alternative embodiment of the invention, shown in FIG. 4, suture tabs 118 with suture holes 116 extend from one or both sides of cuff body 104.

Several stabilizing mechanisms can be used, including suture tabs and holes, staples, ties, surgical adhesives, bands, hook and loop fasteners, and any of a variety of coupling mechanisms. FIGS. 3 and 4, for example, illustrates suture tabs and holes that can be fixed to the surrounding sheath with either absorbable sutures for soft tissue or sutures demanding rigid fixation.

FIG. 5 illustrates sutures 120 that clamp or secure cuff body 104 with device 108 to a surgeon-elected tension. Sutures 120 can be tightened or loosened depending on the level of desired stability and anatomical concerns. As shown in FIG. 5, a gap 122 can be present so long as cuff adapter 100 is sufficiently secured to nerve 102, with a limit set to a nerve diameter to prevent compression of the vasculature within nerve 102. Surgical adhesives (not shown) can be used in combination with sutures 120 on surrounding tissues that move in unison with the neural tissue.

Muscle movement against cuff adapter 100 can also transfer undesired stresses on nerve 102. Therefore, in an embodiment of the invention, low friction surfaces and/or hydrophilic coatings can be incorporated on one or more surfaces of cuff body 104 to provide further mechanisms reducing or preventing adjacent tissues from upsetting the stability of nerve cuff 100.

Figure 6:
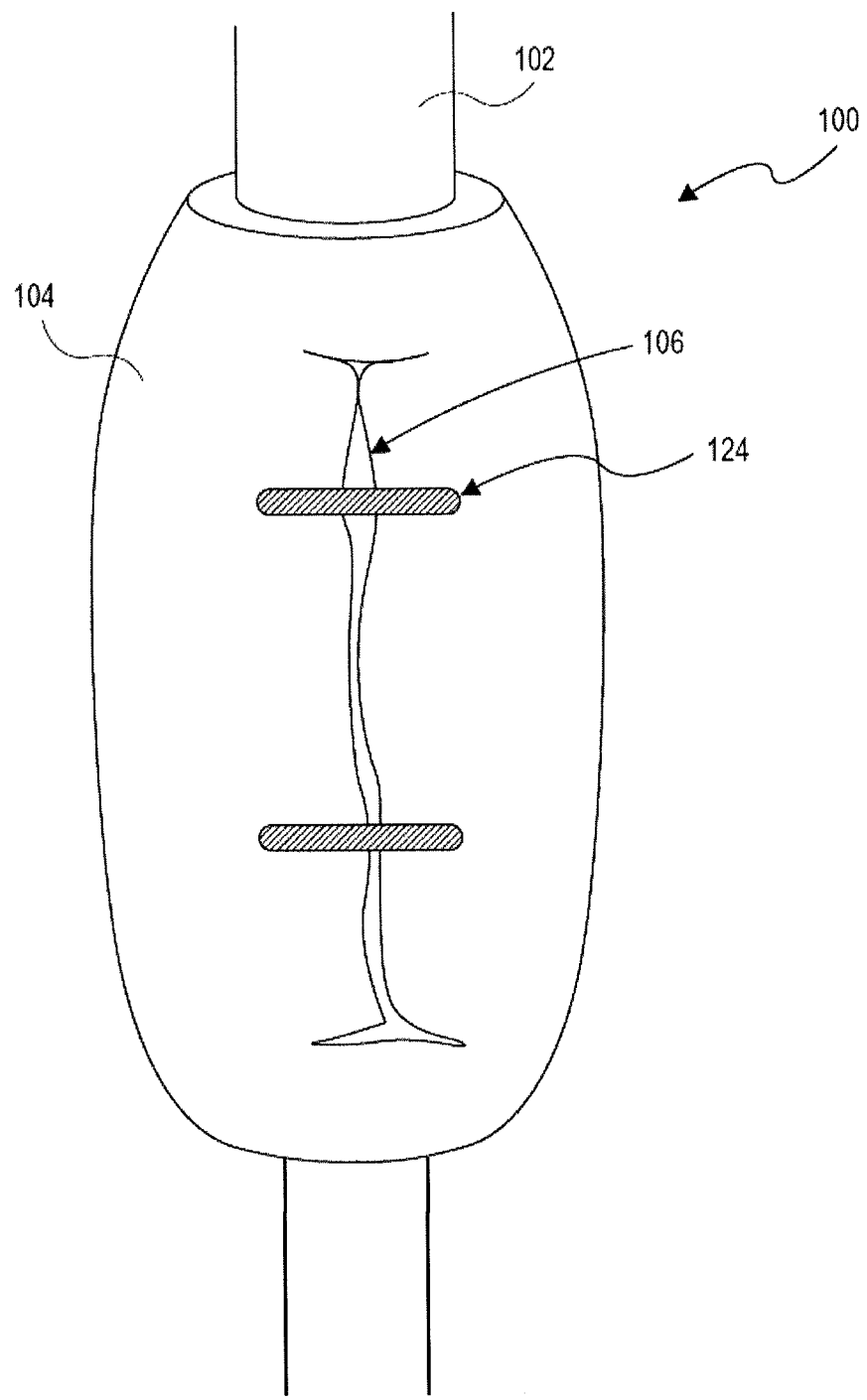
FIG. 6 is a perspective view depicting marsupializaton of the stimulation device within a pocket of the nerve cuff of FIG. 1.

FIG. 6 illustrates a nerve cuff 100 with a stimulator device removably or marsupially secured within pocket or pouch 106 of cuff body 104. By the use of recloseable pouch 106, active stimulator device 108 can be removed or replaced from cuff body 104 without threatening or endangering the surrounding anatomical structures and tissues. Device 108 can be secured within cuff body 104 by any of a variety of securing devices 124, such as, for example, sutures, staples, ties, zippers, hook and loop fasteners, snaps, buttons, and combinations thereof. Sutures 124 are shown in FIG. 6. Releasing sutures 124 allows access to pouch 106 for removal or replacement of device 108. Not unlike typical cuff style leads, a capsule of connective tissue can naturally encapsulate nerve cuff 100 over time. Therefore, it will most likely be necessary to palpate device 108 to locate device 108 and cut through the connective tissue capsule to access sutures 124 and device. The removable/replaceable feature of nerve cuff 100 is advantageous over other cuff style leads because such leads cannot be removed due to entanglement with the target nerve and critical vasculature.

As discussed supra, compression of nerve 102 must be carefully controlled. Excess compression on nerve 102 can lead to devascularization and resulting death of the neural tissue. Compression can be controlled by over-sizing or rightsizing nerve cuff 100, so that when pocket sutures 124 are maximally tightened, the nerve diameter is not reduced less that the measured diameter. Cuffs formed from Silastic™ or Tecothane™ materials are relatively low cost, and therefore several sizes can be provided to the surgeon performing the implantation of nerve cuff 100 to better avoid nerve compression.

Figure 7A:
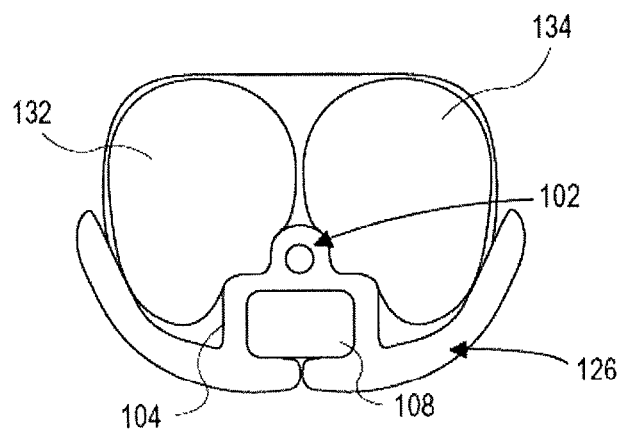
FIG. 7A is a top view depicting a nerve cuff having a conforming shield according to an embodiment of the invention.
Figure 7B:
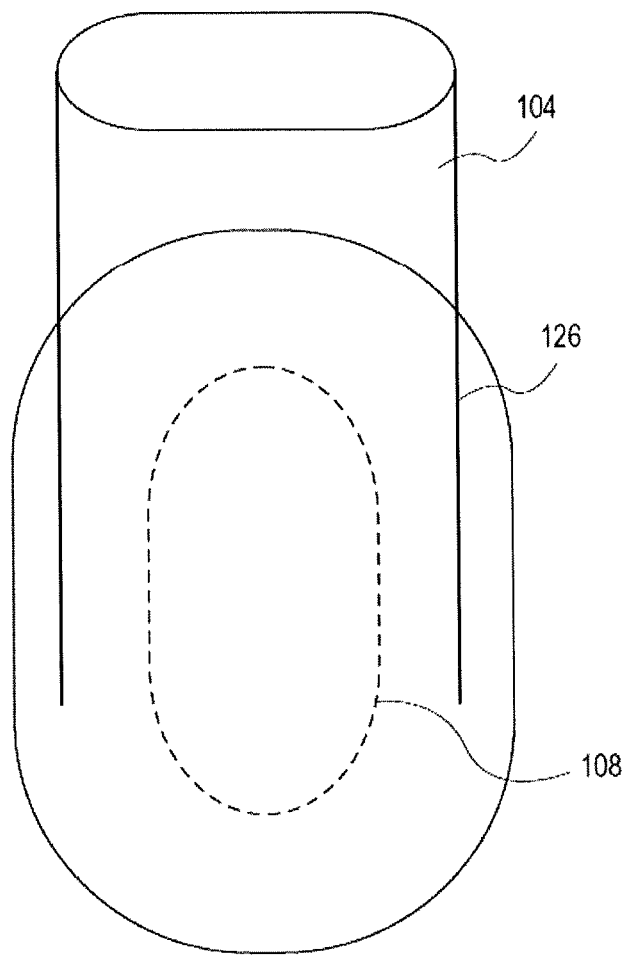

Miniature stimulators, such as device, are still large enough to be felt and palpated by patients as are state-of-the-art commercial cuff systems. Referring to FIG. 7, to avoid such palpation, nerve cuff 100 can further comprise a protecting shield 126 conforming to the shape of the anatomical structures, such as in the carotid sheath. In this embodiment, nerve cuff 100 is secured around the vagus nerve, while isolating device 108 from contact with both the internal jugular vein (IJV) 132, and common carotid artery 134. Shield 126 then further isolates device 108 from other surrounding tissues. It is critical to minimize the profile of the entire cuff adapter 100 while maintaining the compliance of such materials as Silastic™ or Tecothane™. In one embodiment of the invention, protective shield 126 is formed from a PET material, such as Dacron®, optionally coated with Silastic™ or Tecothane™ forming a thin and compliant structure that will allow for tissue separation when required.

Figure 8A:
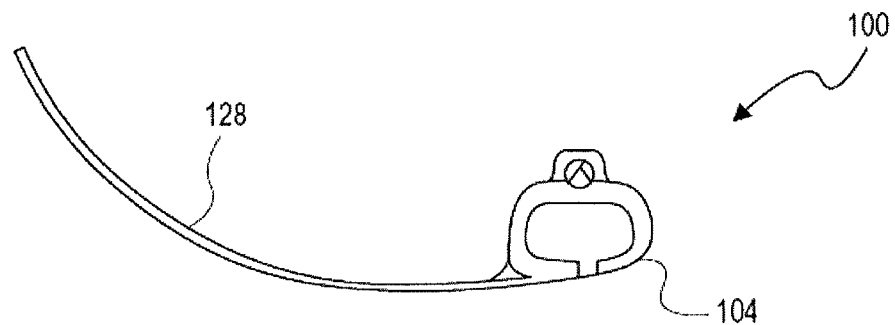
FIG. 8A is a top view depicting an open nerve cuff according to an embodiment of the invention.
Figure 8B:
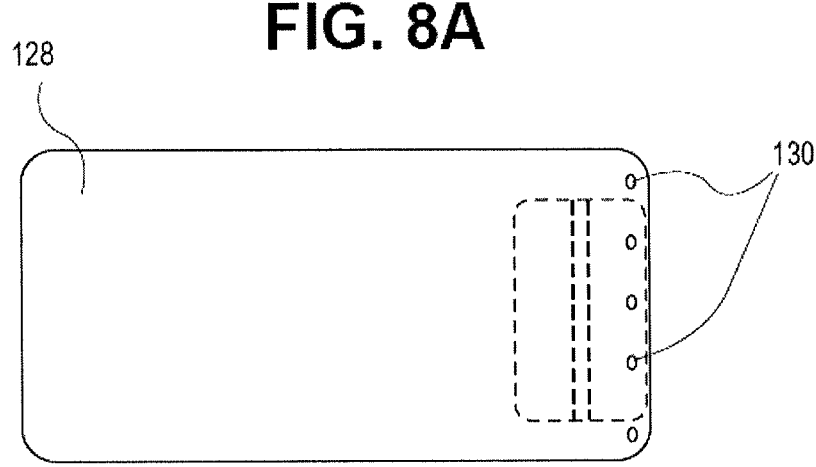
Figure 8C:
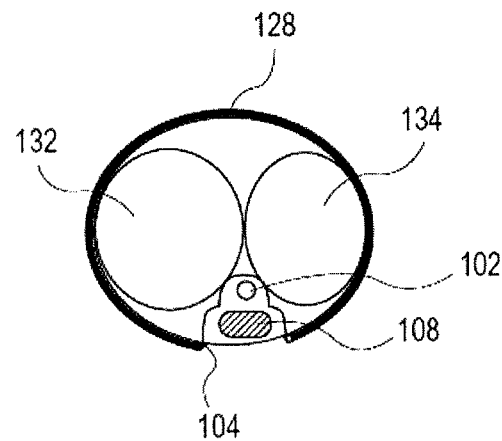
FIG. 8C is a top view depicting the nerve cuff of FIG. 8 in a closed configuration.

When a nerve does not provide sufficient structural strength to support nerve cuff adapter 100, collateral structures can be included in or on cuff body 104. Because of a high degree of anatomical variance such a scheme must demand the skill of the surgeon to utilize a highly customizable solution. FIG. 8a illustrates a variable size nerve cuff 100 with a wrappable retainer portion 128 extending from cuff body 104. As shown in FIG. 8c, cuff body 104 is secured around nerve 102, while retainer portion 128 is secured around the sheath or other surrounding anatomical structures, such as the IJV 132 and/or carotid artery 134. As shown in FIG. 8b, wrappable retainer portion 128 can include securing devices 130, such as suture holes, for securing the entire nerve cuff 100 around the desired anatomical structures. This configuration allows for access to device 108 through pocket 106 as in previous embodiments, while adapting to a multitude of anatomical variations to obtain the desired stability of nerve cuff 100 on nerve 102.

FIGS. 10A-10D illustrate a variation of a nerve cuff that includes a cuff body forming a channel (into which a nerve may be fitted) and an slit formed along the length of the nerve cuff body. In this example, the nerve cuff body also includes a pocket region within the cuff body positioned above the nerve channel. The top of the body (opposite from the nerve channel) includes a long slit 1003 along its length forming on opening. The cuff body may be along the slit by pulling apart the edges, which may form one or more flaps. In the example shown in FIG. 10A, the slit may be split open to expose the inside of the nerve cuff and allow the nerve to be positioned within the internal channel, so that the cuff is positioned around the nerve. The same split may be used to insert the microcontroller as well. In some variations a separate opening (slit or flap) may be used to access the pocket or pouch for the microcontroller.

FIG. 10B shows a perspective view of the nerve cuff holding a microcontroller after it has been inserted onto a nerve (e.g., the vagus nerve). FIG. 10C shows a side view of the same. FIG. 10D shows a section though the view of FIG. 10C, illustrating then nerve within the channel formed through the nerve cuff, and a microstimulator held snugly within the nerve cuff so that the microstimulator is in electrical communication with the nerve via a shared surface between the two. In some variations, as discussed below, the microstimulator is held in a separate, possibly isolated, compartment and electrical contact with the nerve is made by one or more internal leads that couple the microstimulator with the nerve through an internal contact.

The exemplary cuff shown in FIGS. 10A-10D has a conformal configuration, in which the wall thickness is relatively constant, as can be seen from the sectional view in FIG. 10D. In contrast, FIGS. 11A-11D illustrate a variation of a nerve cuff in which the wall thickness varies along the perimeter. This non-uniform thickness may effectively cushion the device relative to the surrounding tissue, even as the patient moves or palpitates the region. This may have the added benefit of preventing impingement of the nerve. Similarly, the variable thickness may enable smooth transitions and help conform the cuff to the surrounding anatomy.

Figure 11A:
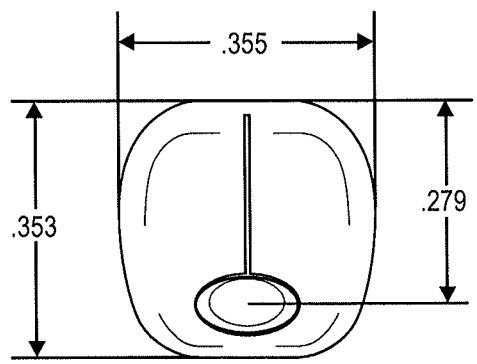
FIGS. 11A-11D illustrate another variation of a nerve cuff.
Figure 11B:
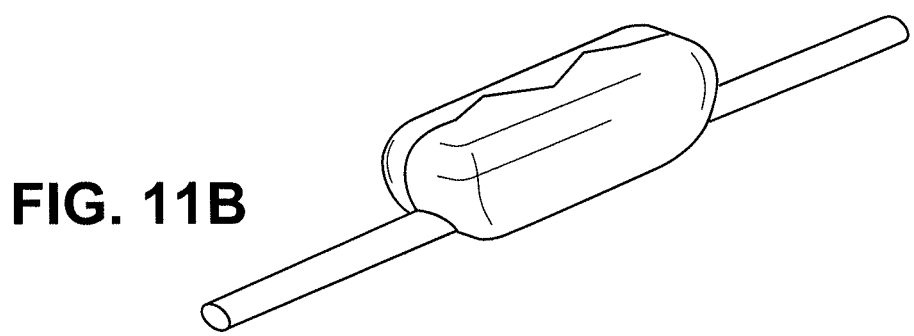
Figure 11C:
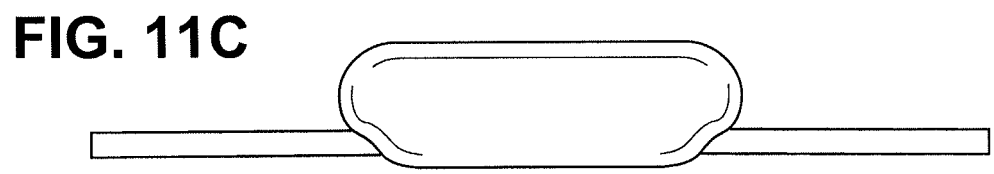

For Example, FIG. 11A shows an end view (with exemplary dimensions illustrated). It should be noted that in any of the figures or examples provided herein, the dimensions shown or described are for illustration only. In practice the dimensions may be +/−some percentage of the values shown (e.g., +/−5%, 10%, 15%, 20%, 25%, 30%, 40%, 50%, etc.). The section through the device shown in FIG. 11D illustrates the non-uniform thickness of the walls.

Both nerve cuff variations shown in FIGS. 10A-10D and FIGS. 11A-11D are substantially rounded or conforming, and have non-traumatic (or atraumatic) outer surfaces. As mentioned, this relatively smooth outer surface may enhance comfort and limit encapsulation of the nerve cuff within the tissue.

Figure 11D:
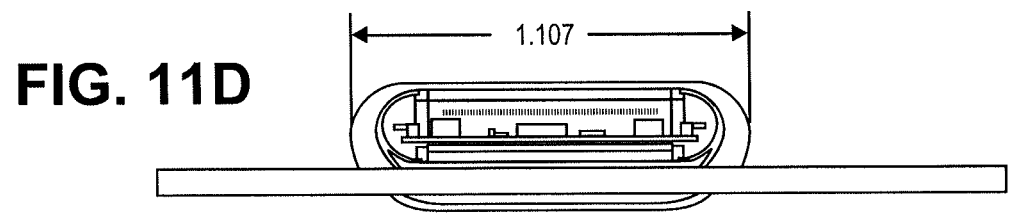
Figure 12:
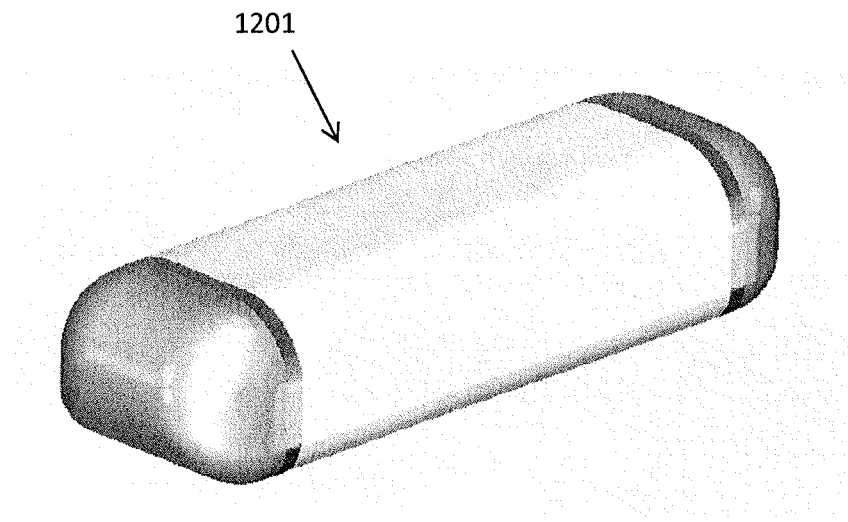
FIG. 12 shows one variation of a microstimulator that may be used in the nerve cuffs described herein.
Figure 13A:
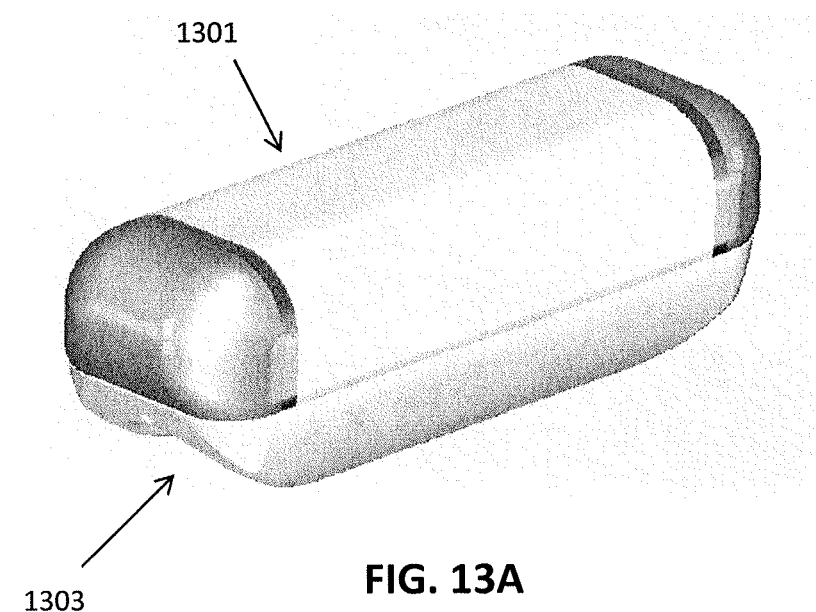
FIG. 13A shows a perspective view of another variation of a microstimulator that may be used as described herein.
Figure 13B:
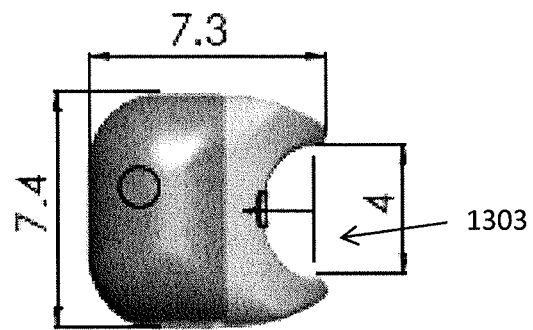
FIGS. 13B and 13C are end and bottom views, respectively, of the microstimulator shown in FIG. 13A.
Figure 13C:
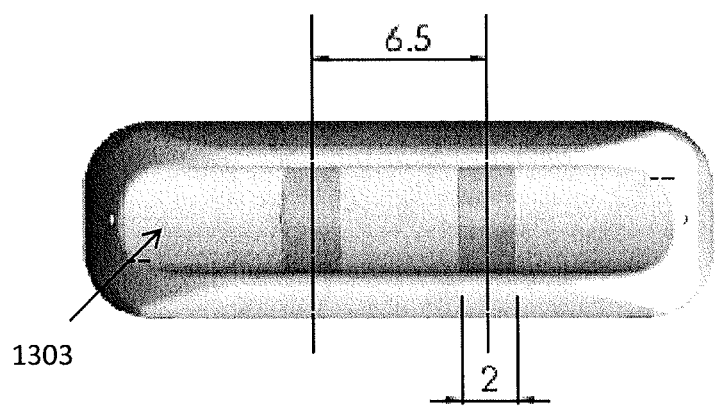

As can be seen from FIGS. 10D and 11D, the microstimulator typically rests above (in the reference plane of the figure) the length of the nerve when inserted into the nerve cuff. In some variations, the microstimulator includes a contoured outer surface onto which one or more contacts (for contacting the nerve or an internal conductor within the nerve cuff) are positioned. For example, FIG. 12 illustrates one variation of a microstimulator 1201. In this example, the microstimulator includes one or more contacts on its outer surface with which to provide stimulation to a nerve. FIG. 13A shows another variation of a microstimulator 1301 in which the outer surface (the bottom in FIG. 13A) is curved to help form a channel surrounding the nerve when the microstimulator is inserted into the nerve cuff. FIG. 13B shows an end view, illustrating the channel concavity 1303 extending along the length of the microstimulator, and FIG. 13C shows a bottom view, looking down onto the channel region. In practice, the microstimulator shown may be placed within the nerve cuff and be held in position at least partially around the nerve. Thus, the microstimulator may help protect the nerve, which may lie within this channel. As mentioned above, and described in greater detail below, it is not necessary that the nerve lie against the contacts, as current may be conducted to the nerve from within the nerve cuff, which may be insulated sufficiently to prevent excessive leak or spillover of the current even when the cuff is oversized and only loosely surrounds the nerve. Furthermore, the nerve cuff may include one or more internal contacts allowing the current from the microstimulator to be distributed to the nerve via one or more internal contacts or leads, including circumferentially around the nerve.

Figure 14A:
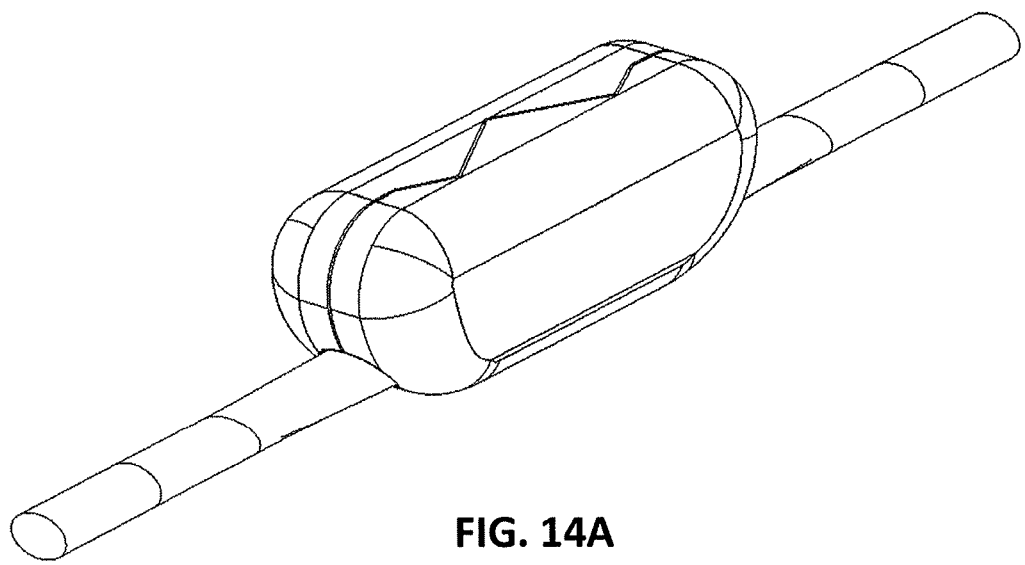
FIGS. 14A and 14B illustrate side and end views, respectively of another variation of a nerve cuff.
Figure 14B:
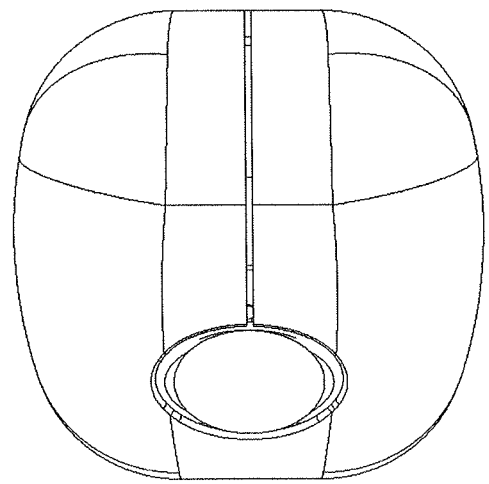

FIGS. 14A and 14B show another variation of a nerve cuff. In this example, the slit forming the opening is positioned on the upper surface (opposite to the nerve channel) along the length of the device. The slit is formed in an interlocking pattern. In FIG. 14a, the slit forms a zig-zag pattern, although other interlocking patterns may be used. For example, a sinusoidal or square-wave pattern may be used. The interlocking pattern may distribute the strain of closing the cuff around the nerve and microstimulator, and may make it easier to close the cuff once it has been positioned and the microstimulator has been inserted. FIG. 14B shows an end view of the same cuff shown in FIG. 14A.

Figure 15A:
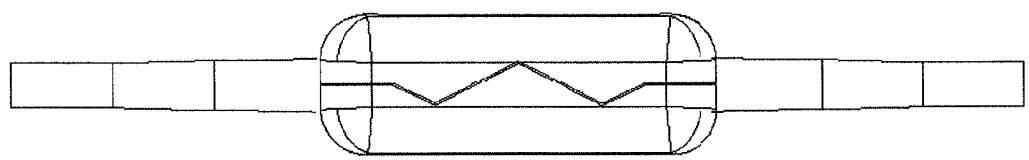
FIGS. 15A-15C show top, side and sectional views, respectively of a nerve cuff such as the one shown in FIG. 14A, attached to a nerve.
Figure 15B:
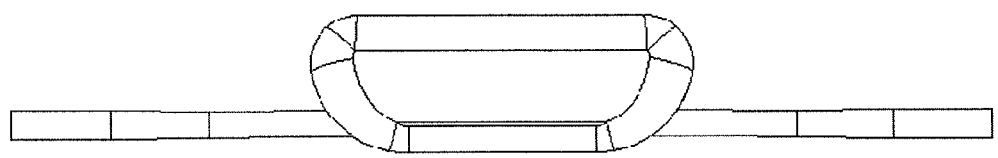
Figure 15C:
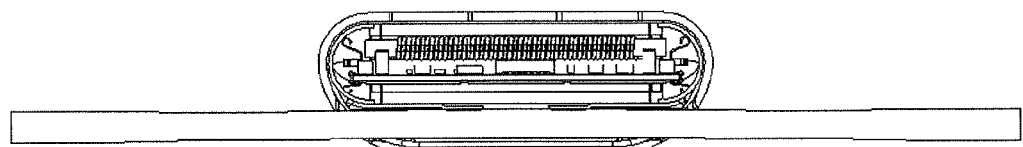
Figure 15D:
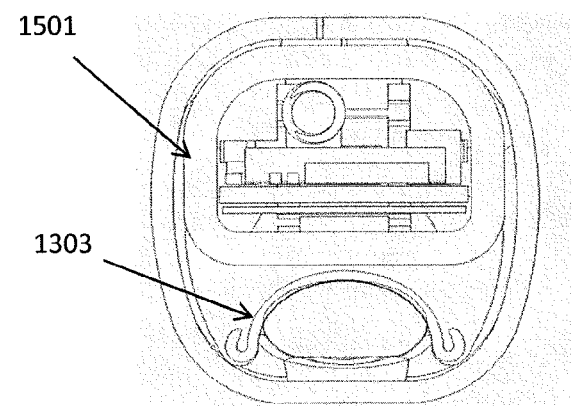
FIG. 15D is a section though the middle of a nerve cuff with a microstimulator secured there.
Figure 16:
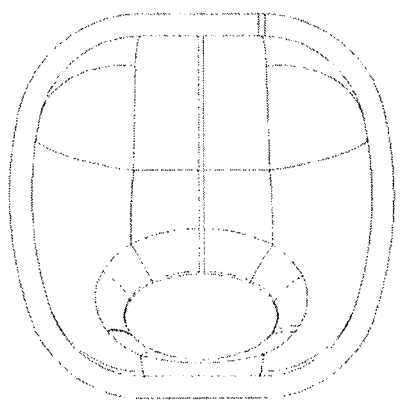
FIG. 16 is an internal end view of a microstimulator similar to the ones shown in FIGS. 14A-15D.

FIGS. 15A-15C show a similar cuff to the one shown in FIG. 14A from top and side views, connected to a nerve. In these example, the nerve extends through the internal channel and out the openings (which may be oval shaped, as shown in FIG. 14B) at either end. In FIG. 15C, a section through the length of the device shows that the microstimulator is positioned in the pouch (cavity) above the nerve. The microstimulator may be held in place by the walls of the cuff. A conforming microstimulator (such as the one shown in FIG. 13A-13C) may be used, as illustrated in the cross-sectional view shown in FIG. 15D. The contacts 1503 of the conforming microstimulator are positioned on the bottom of the device.

Figure 17:
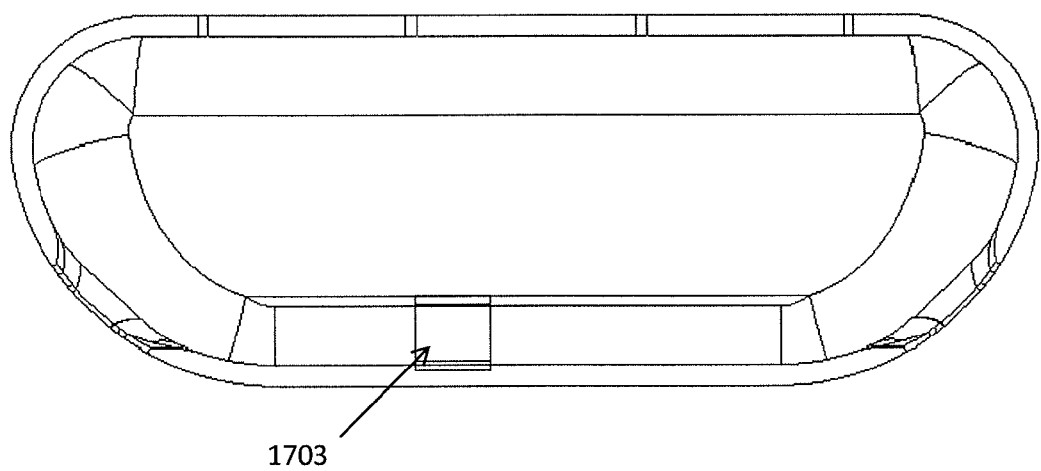
FIG. 17 is a sectional view showing the inside of another variation of a nerve cuff.

As mentioned briefly above, in some variations of the nerve cuff, the inner surface of the cuff body includes one or more internal contacts configured to couple with the microstimulator held within the pouch, and transmit any applied energy to the nerve (or receive energy from the nerve) positioned within the channel through the nerve cuff. The internal lead may be positioned so that it applies current to the underside (along the bottom region of the channel), or around the sides of the nerve as it sits within the channel. In some variations the internal conductor or lead is configured around the channel so that the nerve may be circumferentially stimulated, optimizing the applied stimulation. FIG. 17 is a long section though a nerve cuff, showing the inside of the cuff, and illustrates a variation of a nerve cuff having an internal lead 1703 that may apply stimulation to the underside of the nerve. This internal lead may be formed of any biocompatible conductive material, including medals, conductive plastics, or the likes. The internal lead may include exposed electrode surfaces 1703 for making contact with the nerve. Electrodes may be active contacts, also formed of any appropriate conductive material (e.g., metals, conductive polymers, braided materials, etc.). In some variations, the internal lead is coated or treated to help enhance the transfer of energy between the microstimulator and the nerve. Circumferential stimulation or conduction around the lead may reduce the impedances and assure uniform cross-sectional stimulation of the nerve bundle.

Figure 19:
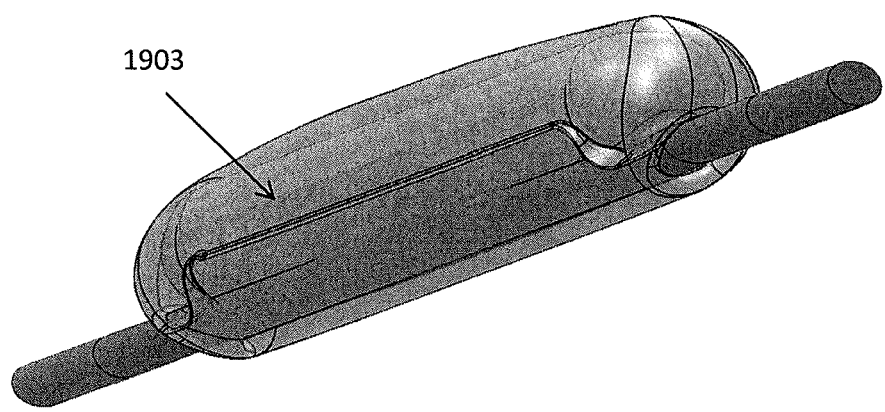
FIG. 19 is a side perspective view of a side-opening nerve cuff.

FIG. 19 shows another variation of a nerve cuff as described herein. In this example, the nerve cuff includes slit 1903 along one side of the device, adjacent to the nerve channel, which can be opened (e.g., by pulling apart the flaps or sides of the cuff) to expose nerve channel and the pocket for the microstimulator.

Figure 18:
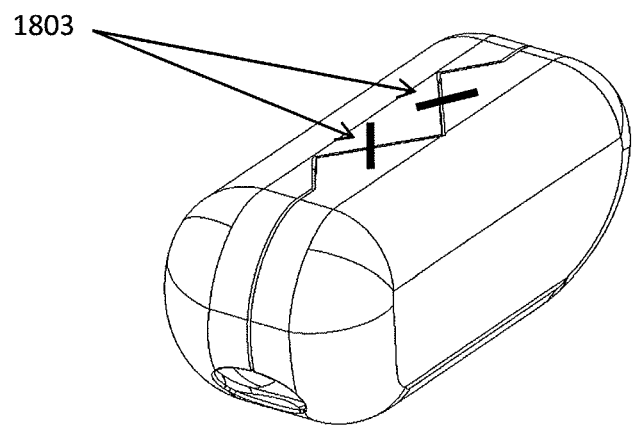
FIG. 18 is a side perspective view of the top-opening nerve cuff shown in FIG. 17.

Many of the nerve cuff variations described herein may be opened and positioned around the nerve, for example, by splitting them open along a slit or hinge region. The device may be configured so that they have sufficient resiliency to close themselves, or remain closed if the edges of the slit region are brought together. Thus, the device may have a shape memory property that encourages them to close. In some variations, as already mentioned, it may be useful to hold them closed, at least temporarily, once they have been positioned over a nerve and the microstimulator has been positioned within the pocket. Thus, the device may include one or more closure elements. For example, the device may include a suture hole or passage for suturing the device closed. In some variations the nerve cuff includes a button or other fastener element. In some variations, as illustrated in FIGS. 6 and 18, the device may be sutured close with a dissolvable suture. A few weeks or months after insertion, the nerve cuff may be encapsulated or engulfed by the surrounding tissue, and will be held closed by this encapsulation. Thus, the dissolvable sutures merely keep the cuff closed for initial anchoring before biointegration and encapsulation occurs.

Figure 21:
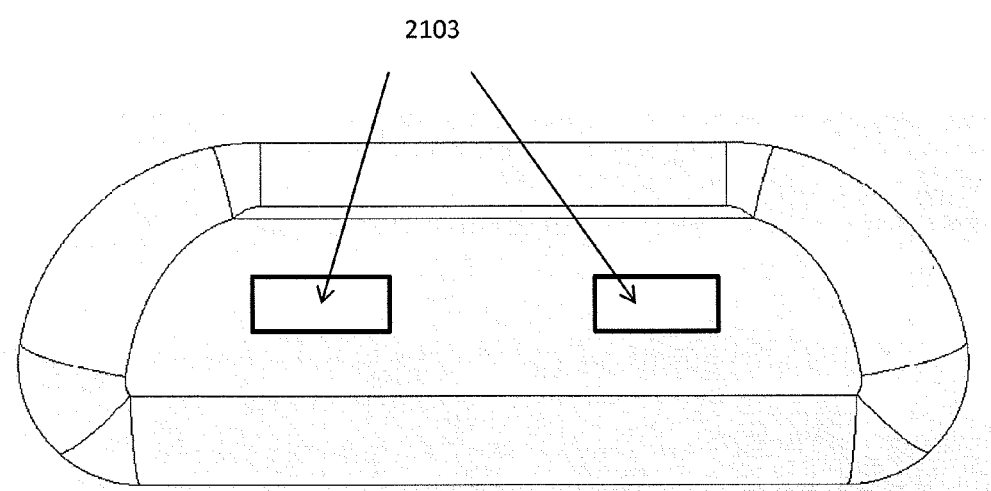
FIG. 21 is a side view of another variation of a nerve cuff.

Any of the nerve cuffs described herein may also include one or more external leads or contacts facing the outside of the nerve cuff body, which may be used to stimulate tissues outside of the nerve cuff, and not just the nerve within the channel through the cuff. FIG. 21 illustrates one variation of a nerve cuff having external leads. In this example, the nerve cuff includes two external contacts 2103 that are connected (through the wall of the nerve cuff body) to the microstimulator held within the nerve cuff pocket. Such external leads may be used for sensing in addition to (or instead of) stimulation. For example, these electrical contacts may be used to sense other physiological events such as muscle stimulation and/or cardiac function. These signals can be applied to aid synchronization of target nerve stimulation to minimize artifacts of target stimulation. Such signals may be too faint for reliable remote sensing, however the position of the microstimulator (insulated within the housing of the nerve cuff) may allow accurate and reliable sensing.

Figure 20:
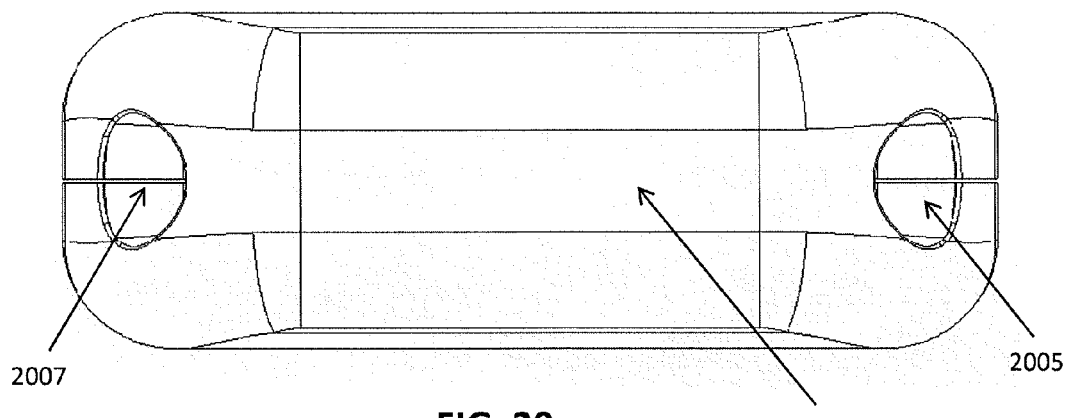
FIG. 20 is a transparent view of the bottom of a nerve cuff, showing the nerve channel.

A nerve may sit within a supported channel through the nerve cuff. As illustrated in FIG. 20, the channel 2003 may be formed having generally smooth sides, so as to prevent damage to the nerve and associated tissues. In some variations the nerve channel though the cuff is reinforced to prevent the cuff from pinching the device or from overtightening the device when closed over the nerve. Supports may be formed of a different material forming the nerve cuff body, or from thickened regions of the same material. Although multiple sizes of nerve cuff may be used (e.g., small, medium, large), in some variations, an oversized nerve cuff may be used, because the insulated cuff body will prevent leak of current from the microstimulator to surrounding tissues.

In general, the nerve cuff body may be electrically insulating, preventing leakage of charge from the microstimulator during operation. In some variations the nerve cuff includes shielding or insulation sufficient to electrically insulate the microstimulator within the nerve cuff body. Shielding material may particularly include electrically insulative materials, including polymeric insulators.

Figure 23:
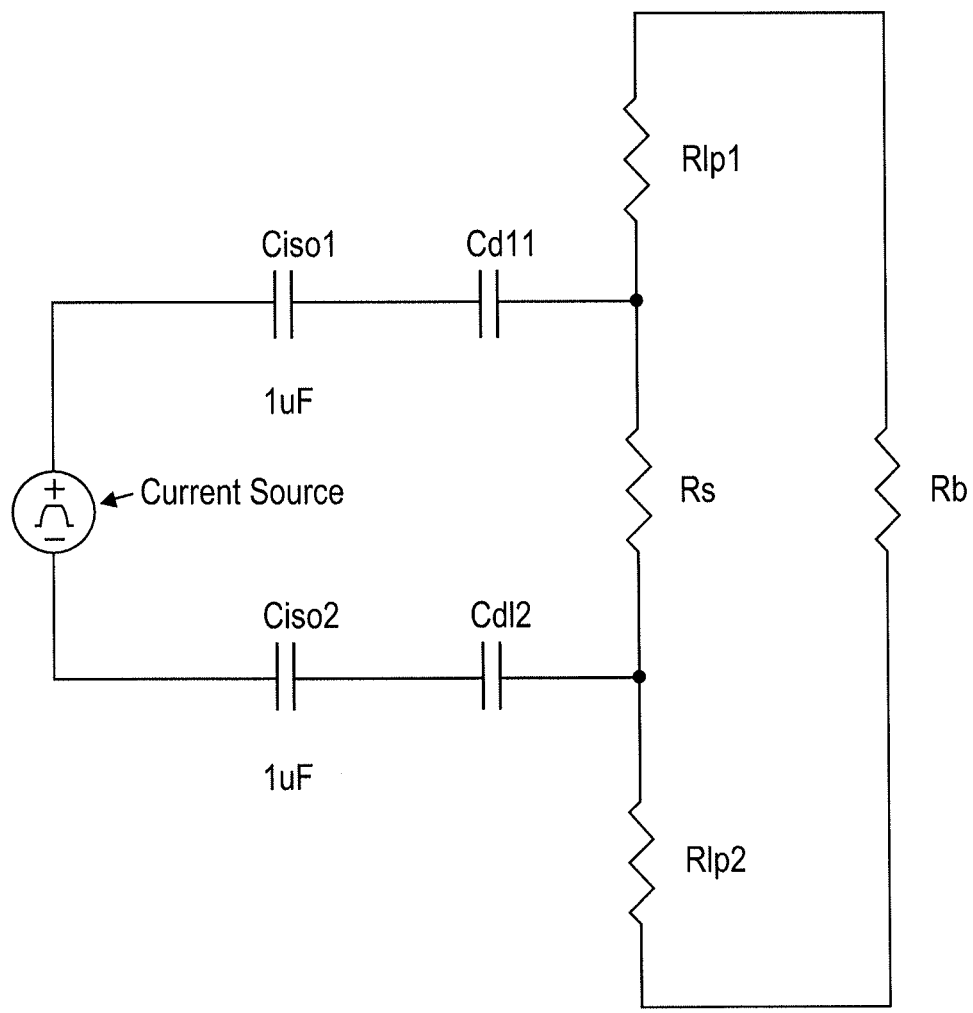
FIG. 23 shows an equivalent circuit modeling current loss when the nerve cuff is only loosely arranged over the nerve.

It may be shown mathematically using an equivalent circuit of the microstimulator, as shown in FIG. 23, that the current from a microstimulator is not appreciably passed out of even a loosely applied nerve cuff. This allows for the use of oversized nerve cuffs, rather than requiring rigorous sizing, or risking constricting the nerve.

For example, assuming a nerve with a cross section of $N_{area}$ is surrounded by a column of fluid $F_{area}$ enclosed by the nerve cuff, where contacts on the inside the microstimulator are spaced $E_{spacing}$ apart (center to center) and have a width $E_{width}$ and circle around the column of fluid and nerve $E_{degrees}$, it can be shown that the current will leak out the ends through a distance between the center of the electrode and the end of the nerve cuff that is defined by a distance $D_{guard}$.

The electrical model (illustrated in FIG. 23) consists of a current source that drives through DC isolation capacitors ($C_{iso2}$ optional), through the capacitance of each electrode ($C_{dl1}$ and $C_{dl1}$). From the electrodes, the current passes through either path $R_S$ or $R_{ip1}+R_b$ $R_{ip2}$. Where as a portion of the current passing through $R_s$ provides useful work and the current passing through $R_{ip1}+R_b+R_{ip2}$ passes outside of the device and may cause undesirable effects.

If the nerve has a tight fit, then all the current passing through $R_s$ would contribute towards stimulation, but only a portion of the current can activate the nerve in the case of a loose fit. Based on this model, it can be shown that (assuming that the nerve and fluid columns form an ellipse defined by the major and minor axis a and b, and the pulse width is short and capacitances are large) just the real impedance and efficiency can be estimated.

The electrode surface area is determined to estimate the complex portion of the impedance: $F_{area}=\pi^*a_F^*b_F$ and $N_{area}=\pi^*a_N^*b_N$.

Assuming the impedance of the cuff contained fluid and nerve has a similar conductance p and electrodes are spaced at $E_{spacing}$ then the real resistance of the conduction volume is: $R_{working}=E_{spacing}^*\rho/F_{area}$, where the wasted resistance that should be maximized is calculated by: $R_{wasted}=2^*D_{guard}^*\rho/F_{area} R_{bulk}$, where $R_{bulk}$ is defined as the free field resistance between the two ends of the cuff.

So the efficiency ($\eta$) of the real current delivered in the POD is $R_{wasted}/(R_{working}+R_{wasted})$, and for the case of an undersized nerve assuming the conductivity of tissue and the fluid column is about equivalent then the stimulation efficiency is defined as $\eta_T=\eta^*N_{area}/F_{area}$.

Methods of Insertion

Figure 22A:
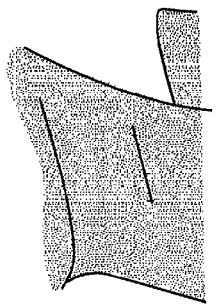
FIGS. 22A-22H illustrate steps for inserting a nerve cuff such as the nerve cuffs described herein.
Figure 22B:
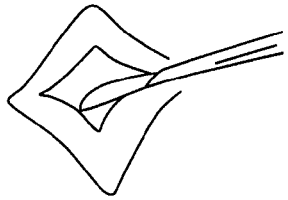
Figure 22C:
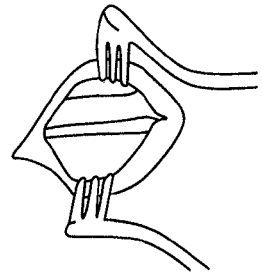
Figure 22D:
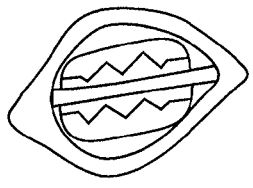
Figure 22E:
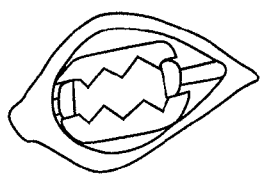

In operation, any of the devices described herein may be positioned around the nerve, and the microstimulator inserted into the nerve cuff, in any appropriate manner. FIGS. 22A-22H illustrate one variation of a method for applying the nerve cuff around the nerve and inserting a microstimulator. In this example, the patient is prepared for application of the nerve cuff around the vagus nerve to hold a microstimulator device securely relative to the nerve (FIG. 22A). An incision is then made in the skin (≈3 cm) along Lange's crease between the Facial Vein and the Omohyoid muscle (FIG. 22B), and the Sternocleidomastoid is retracted away to gain access to the carotid sheath (FIG. 22C). The IJV is then reflected and <2 cm of the vagus is dissected from the carotid wall.

Figure 22F:
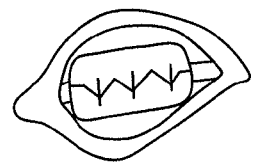
Figure 22G:
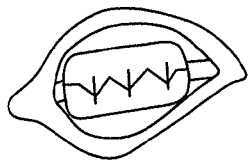
Figure 22H:
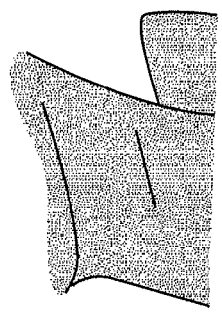

In some variations, a sizing tool may be used to measure the vagus (e.g., diameter) to select an appropriate microstimulator and cuff (e.g., small, medium, large). In some variations of the method, as described above, an oversized cuff may be used. The nerve cuff is then placed under the nerve with the opening into the nerve cuff facing the surgeon (FIG. 22D), allowing access to the nerve and the pocket for holding the microstimulator. The microstimulator can then be inserted inside cuff (FIG. 22E) while assuring that the microstimulator contacts capture the vagus, or communicate with any internal contacts/leads. The nerve cuff may then be sutured shut (FIG. 22F). In some variations, the microstimulator may then be tested (FIG. 22G) to confirm that the device is working and coupled to the nerve. For example, a surgical tester device, covered in a sterile plastic cover, may be used to activate the microstimulator and perform system integrity and impedance checks, and shut the microstimulator off. If necessary the procedure may be repeated to correctly position and connect the microstimulator. Once this is completed and verified, the incision may be closed (FIG. 22H).

The invention may be embodied in other specific forms without departing from the essential attributes thereof; therefore, the illustrated embodiments should be considered in all respects as illustrative and not restrictive. The claims provided herein are to ensure adequacy of the present application for establishing foreign priority and for no other purpose.

What is claimed is:

1. A nerve cuff for enclosing a leadless microstimulator in stable communication with a nerve, the nerve cuff comprising:
    a flexible cuff body having a first end, a second end, and a nerve channel extending within the length of the cuff body from the first end to the second end for passage of a nerve;
    a pocket within the cuff body, configured to removably hold the leadless microstimulator; and
    an elongate opening slit extending the length of the cuff body configured to be opened to provide access to the pocket and the channel, and configured to be closed around the pocket and channel, enclosing the cuff body around the nerve.

2. The nerve cuff of claim 1, further comprising an external electrical contact on the outer surface of the cuff body configured to couple with the microstimulator.

3. The nerve cuff of claim 1, wherein the cuff body has a uniform thickness.

4. The nerve cuff of claim 1, wherein the cuff body has a non-uniform thickness.

5. The nerve cuff of claim 4, wherein the cuff body has a thickness between about 5 and about 20 mils.

6. The nerve cuff of claim 1, wherein the outer surface of the nerve cuff is substantially smooth and atraumatic.

7. The nerve cuff of claim 1, wherein the outer surface of the nerve cuff is contoured.

8. The nerve cuff of claim 1, wherein the channel comprises a support channel configured to support the nerve within therein, to prevent pinching of the nerve.

9. The nerve cuff of claim 1, wherein the elongate opening slit extends the length of the cuff body in an interlocking pattern.

10. The nerve cuff of claim 1, further comprising attachment sites in the elongate opening slit configured to help secure the slit closed.

11. The nerve cuff of claim 1, wherein the cuff body is formed of a flexible and biocompatible polymer.

12. The nerve cuff of claim 11, wherein the flexible and biocompatible polymer is a silicone based polymer.

13. The nerve cuff of claim 1, further comprising a conductive surface within the nerve channel configured to engage one or more electrical contacts on the microstimulator.

14. The nerve cuff of claim 1, wherein the first end and the second end of the cuff body each have a strain relief element.

15. The nerve cuff of claim 14, wherein the strain relief element is configured to coil around the nerve.

16. The nerve cuff of claim 14, wherein the strain relief element is tapered.

17. The nerve cuff of claim 1, wherein the cuff body further comprises one or more connection elements configured to secure the cuff body to the nerve.

18. The nerve cuff of claim 17, wherein the one or more connection elements is a suture hole or tab.

* * * * *